(12) United States Patent
Clarke

(10) Patent No.: US 9,297,024 B2
(45) Date of Patent: Mar. 29, 2016

(54) RECOMBINANT PROTEIN EXPRESSION USING A HYBRID CHEF1 PROMOTER

(71) Applicant: Howard R. Clarke, Friday Harbor, WA (US)

(72) Inventor: Howard R. Clarke, Friday Harbor, WA (US)

(73) Assignee: CMC ICOS BIOLOGICS, INC., Bothell, WA (US)

( * ) Notice: Subject to any disclaimer, the term of this patent is extended or adjusted under 35 U.S.C. 154(b) by 0 days.

(21) Appl. No.: 14/204,879

(22) Filed: Mar. 11, 2014

(65) Prior Publication Data

US 2014/0273208 A1    Sep. 18, 2014

Related U.S. Application Data

(60) Provisional application No. 61/777,603, filed on Mar. 12, 2013.

(51) Int. Cl.
*C12N 15/85* (2006.01)
*C07K 14/47* (2006.01)

(52) U.S. Cl.
CPC ............ *C12N 15/85* (2013.01); *C07K 14/4702* (2013.01)

(58) Field of Classification Search
None
See application file for complete search history.

(56) References Cited

U.S. PATENT DOCUMENTS

| 5,888,809 A | 3/1999 | Allison |
| 2006/0121574 A1 | 6/2006 | Allison |

FOREIGN PATENT DOCUMENTS

| WO | WO-2005/030969 A1 | 4/2005 |
| WO | WO-2007/081336 A1 | 7/2007 |
| WO | WO-2012/052878 A1 | 4/2012 |

OTHER PUBLICATIONS

Sequence Alignment for SEQ ID No. 2. Mar. 18, 2015, 6 pages.*
Beck et al., the quantitative proteome of a human cell line. *Molec. Syst. Biol.* 7: 549 (2011), 8 pages.
Boshart et al., A very strong enhancer is located upstream of an immediate early gene of human cytomegalovirus. *Cell*, 41: 521-30 (1985).
Hammond et al., Insulin stimulates the translation of ribosomal proteins and the transcription of rDNA in mouse myoblasts. *J. Biol. Chem.* 25: 17785-91 (1988).
Logan et al., Adenovirus tripartite leader sequence enhances translation of mRNAs late after infection. *Proc. Natl. Acad. Sci USA*, 81: 3655-9 (1984).
Mariottini et al., The 5' untranslated region of mRNA for ribosomal protein S19 is involved in its translational regulation during Xenopus development. *Mol. Cell. Biol.* 10: 816-22 (1990).
Proud et al., Molecular mechanisms for the control of translation by insulin. *Biochem. J.* 328: 329-41 (1997).
Running Deer et al., High-level expression of proteins in mammalian cells using transcription regulatory sequences from the Chinese hamster EF-1 alpha gene. *Biotechnol. Prog.* 20: 880-9 (2004).
Sanders et al., Elongation factor-1 messenger-RNA levels in cultured cells are high compared to tissue and are not drastically affected further by oncogenic transformation. *Nucl. Acids Res.* 20: 5907-10 (1992).
Thomas et al., Translational control of mRNA expression during the early mitogenic response in Swiss mouse 3T3 cells: identification of specific proteins. *J. Cell Biol.* 103: 2137-44 (1986).
International Search Report and Written Opinion for Application No. PCT/US2014/023661 dated Aug. 14, 2014, 9 pages.

* cited by examiner

*Primary Examiner* — Anne Gussow
*Assistant Examiner* — Channing S Mahatan
(74) *Attorney, Agent, or Firm* — Marshall, Gerstein & Borun LLP

(57) ABSTRACT

The invention provides expression vectors and host cells for high-level expression of recombinant proteins. The expression vectors comprise Chinese hamster ovary elongation factor 1-α (CHEF1) transcriptional regulatory DNA elements and a cytomegalovirus (CMV) promoter and/or a human adenovirus tripartite leader (AdTPL) sequence. The invention achieves increased protein expression and better productivity of host cells compared to previously described expression systems.

20 Claims, 10 Drawing Sheets

Figure 4
Figure 4A
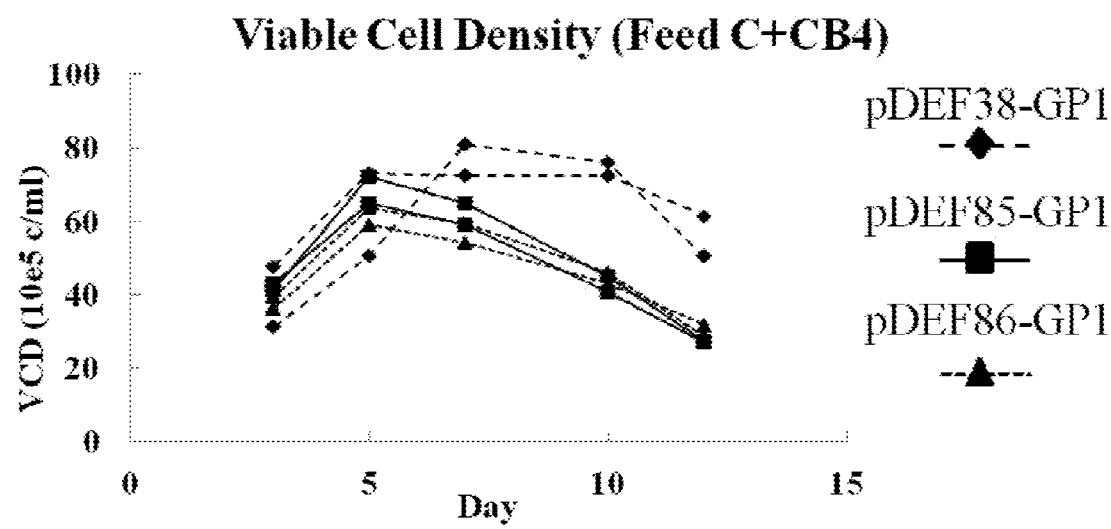
Figure 4B
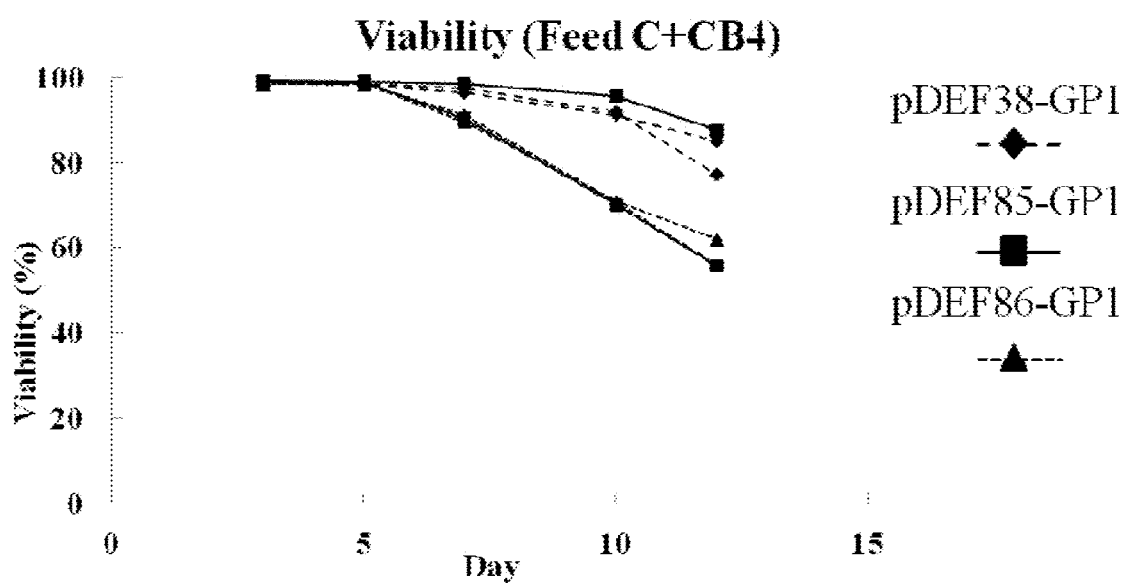

Figure 7
Figure 7A
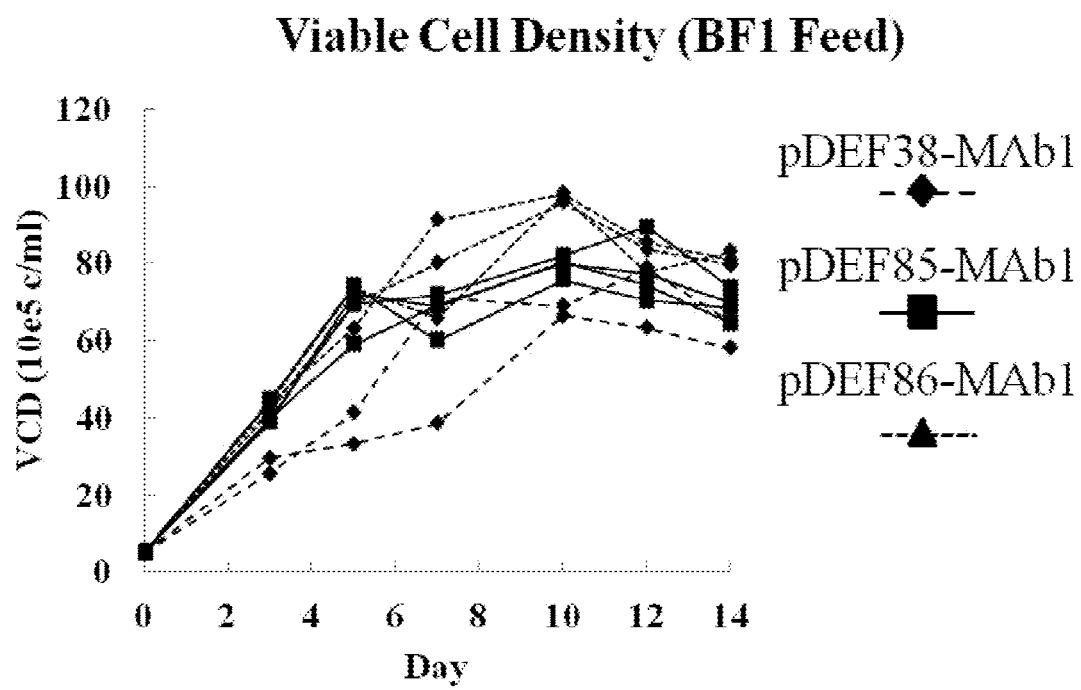
Figure 7B
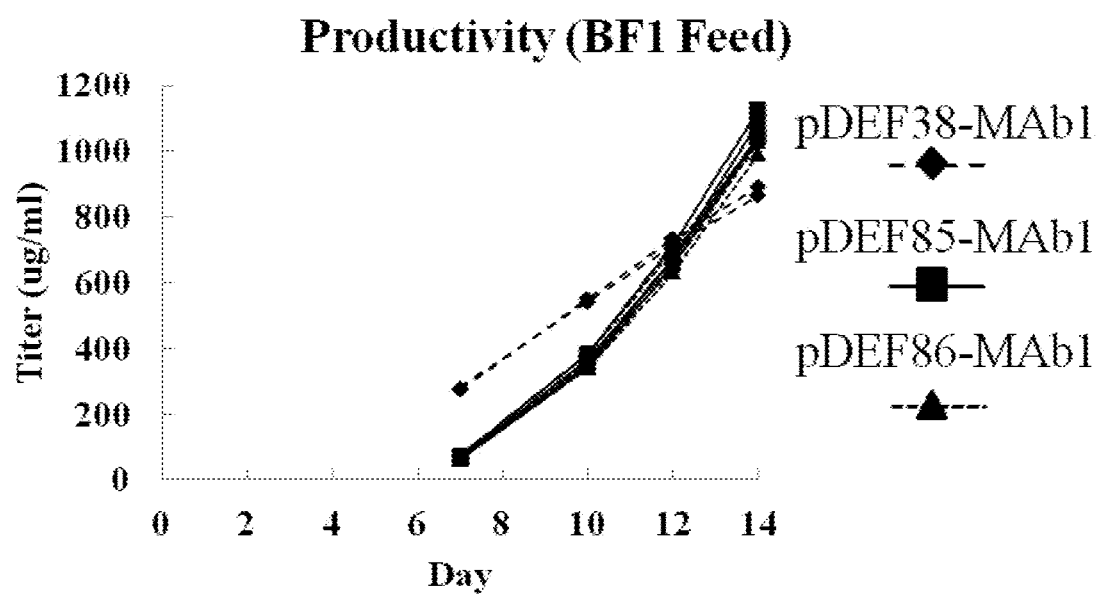

Figure 8
Figure 8A
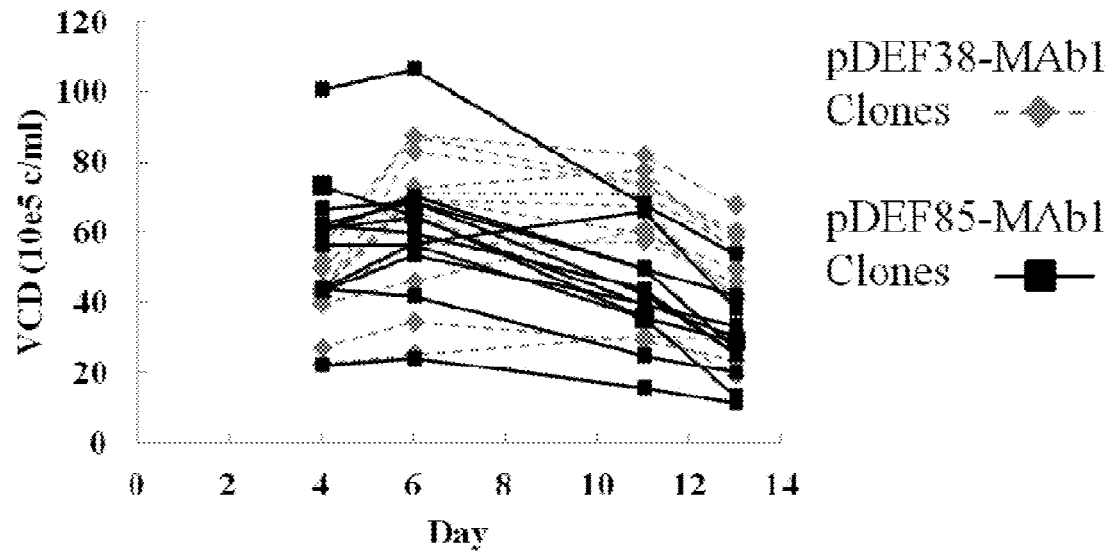
Figure 8B
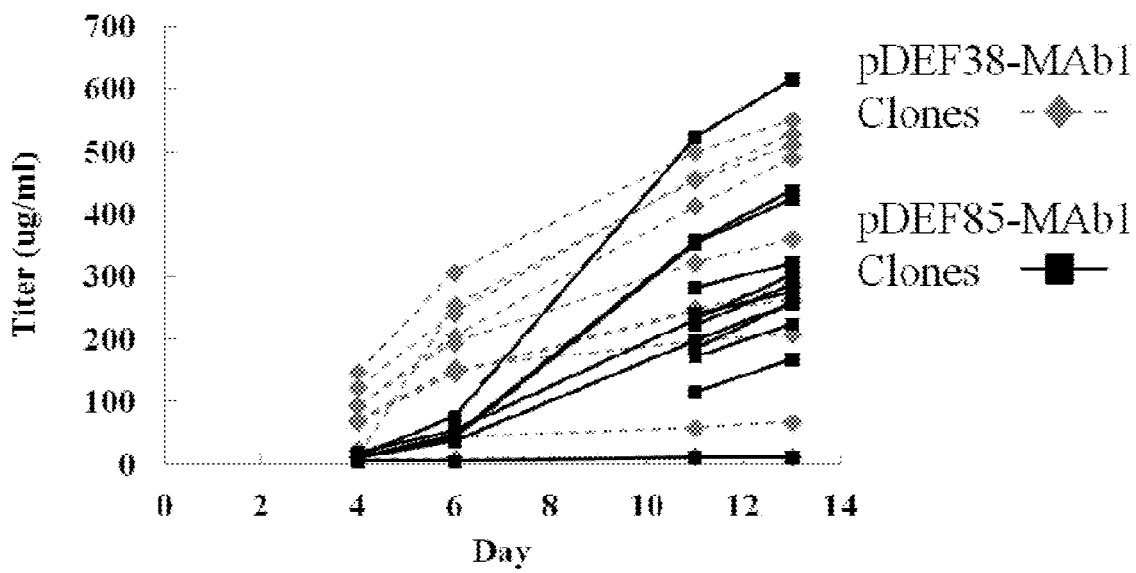

Figure 9
Figure 9A
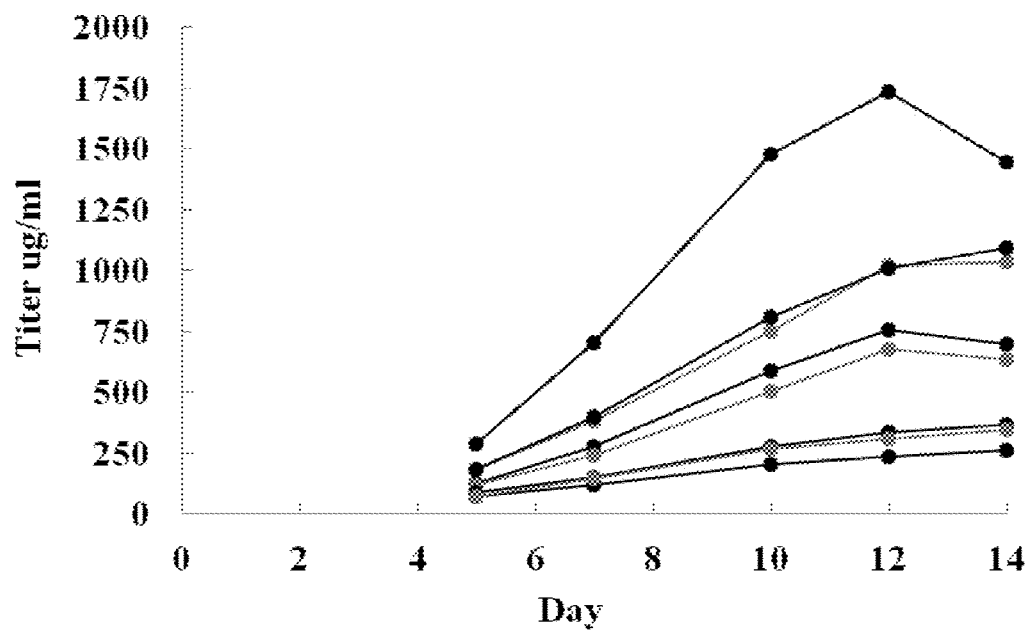
Figure 9B
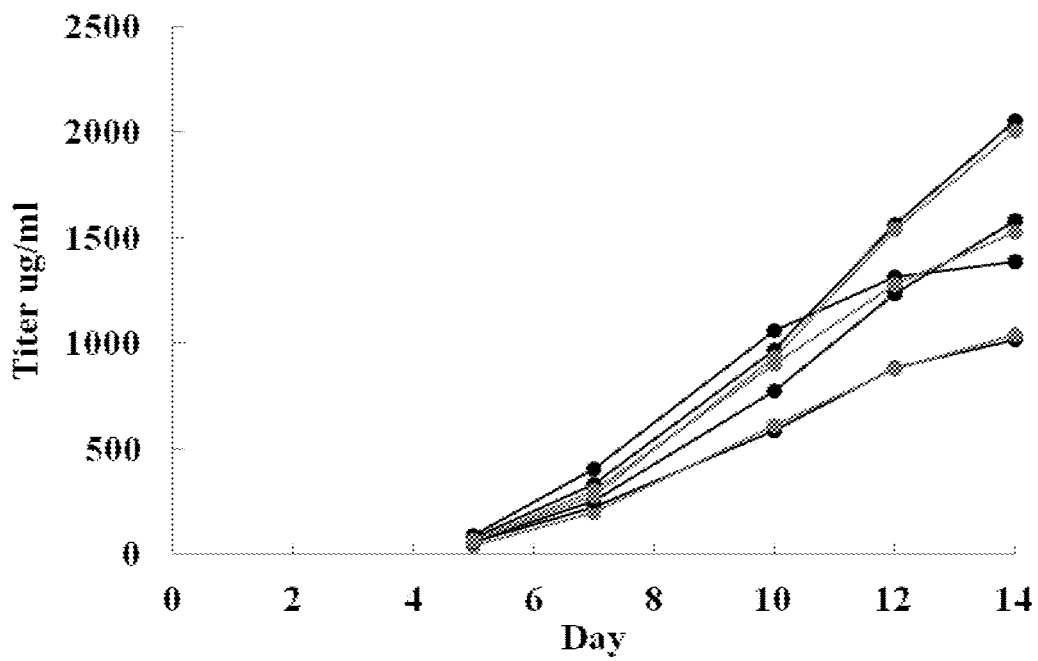

SEQUENCE LISTING

```
<160> NUMBER OF SEQ ID NOS: 7

<210> SEQ ID NO 1
<211> LENGTH: 11716
<212> TYPE: DNA
<213> ORGANISM: Cricetulus griseus

<400> SEQUENCE: 1
ctagaagata tatttgaaat ctttactatt ttgttttctg aaatcacagg acagggctt      60 tgctcttcag cctcgtgggc tctgatactt ttcctcacat ataaagctag ttatttttgg    120
tggatgccat tgagcattta ttattctagt ccagacacag tcagcaaaag ctgctatatg    180
ttgactgaaa ttaagtcaat taaggaaatg aggcaataat gtatgacagt acaggtaaag    240
```

```
gatctgcagt ggctcacagg tgacagacac acaaattgac gtgggggggag aagcaccttt    300 ttttgggggg ggctggttag tttggagttt tgtttattcc ttccttccct ccttcctttc    360
ttcctccctt cccttccctt ccctttccttc cttccttcct tccttcctc cttccttcct    420 tccttccttc ctttctttct ttctttcttt cttttctttct ttctttcttt ctttctgttt    480
ttgtgtattg ctgtgtttta gacaggatct cactatgtag tcctggctgg cctggaactt    540
actatgtaga ccatgctggc ctcagattca cagacacctg tctactcttg cttttttgag    600
gaatgagatt gaatgtatgc accatgaccg atcaggtttt gctgttgttt tagccaggct    660
tgcttaaaat gcaatgtaaa ccttcagcat taggctcctg ggttctagga ttatagtagg    720
tgtaagccat catgcccagc ttgtcactgg tcttaaagat atttatttat tttatgtgta    780 taatttttg cctgtgtgta tgtctgtgca caccatgcat gcctggtgac cgtggagcta    840
aaagagacac tcggaattgg agttgtatta gattgtgagc cgctctgtgg gtgctggaaa    900
ttaaactgtg tcctcaagaa aagcagctag tcctcttaac tgcttagcca tctctctagc    960
cctgtccata ttttcaaata gaataattga actgaaagta cctctctgac tattggtttc   1020
aggattgtac agaataattt gtctgcaatg tcattttaat aaattctgca tacttattgg   1080 aaaacactt tttttaaaac taaactaaaa ttatctttga tactttctc tctcatcaat    1140 atccacttcc cttcatttt ctatatttc agtaccgggg attaaatacc aaggttcttt    1200
taaatactag atttagcta tgactgtacc tcatacaaaa cctcttgtca gctgtcaaga    1260
ggtttgatga tccctggtt cttgttgttg tttgaggttg ttgtttgagc cctgccctgg    1320
ctttcctaga actcacagtg tagaccagta tgaacttgaa ctcacagtga gcgtccaccc    1380
acctgcctct gccttctgag tgctgggact aaaggtgtga accaacattg caggcaggag    1440
gattcttgat tcttttgagag tctgttatta gaaaaagatg ctctaagaat ttaactataa    1500
taacacccag ctgagacctg gttttctctc atgacatatg caaagtttgg gtgttttttt    1560
tcaaccaact ctggaaagtt cctttggcag caggaatagc ttgctaattg atataaggaa    1620
gcagatggta ctagaaaaac agcaacaact aaaaaagata ccatacttcg aaagaaaaaa    1680
gataaatgac atttaaccac agagcacaag tgtgtgtgac aagattttag aattaagggt    1740
gactgtttat gttgctttta aaagacatgt aatttcggga tggtggtggc acacgccttt    1800
aatcccagca ctcgggaggc agaggcaggt ggatctctgt gagttcgaga ccagcttggt    1860
ctacaagagc gagttccagg acagcctcca aagccataga gaaaccctgt ctcaacatcc    1920
cccccccaaa aaaagaatt aggggaactg attatgttgc ttttttaaaag acatgtaact    1980 ttcgtagtgg tggtggcaca tgcctttaat cccagcactt gggtggcaaa ggcaggcaga    2040
tctctgagtg tttaaggaca acctgggtta tatagtgaga atctgttctg tcttttaaaa    2100
aggtgatagt tcactgtaca acctctgaca attatttagt atgttttcat attaccagtt    2160 acttttttt gtttgtttgg ttttttcgaga cagagacagg gtttctctgt gtagctttgg    2220
agcctatcct ggcactcgct ctggagacca gggtggcctc gaactcacag agatccgcct    2280
gcctctgcct tccgagttct gggattaaag gcgtacgcca ccaacgcccg gctaccagtt    2340
acttttaaat gtttataatt gccaggtggt gatcgtgcat gcttttaatc ccagaacttg    2400
gaaggcagag gcaggcctgt gagtttgagg ccagcctggt ataaagggct agttccagga    2460
cagctagggc tattacacag agaaaactctg tttcaaacaa acaaacagaa aaacaacaac    2520
aatttataat taaaaagata cgaatgagtt tttctggact gactcaaaat aatgtcataa    2580
```

```
aacatacaaa ttgagagtag tctttcctca gaagtcctat aggcacatgt cttcctagct    2640
aacaattgta caatgtcact ttatgtcatg gcatattgga actgtgaggt agacgctaag    2700
aataaggagc catctgcttt gtagattcgc ttgagagatc tacaactgcc agttgtcttg    2760
aagtctgaac aaaggcaagt gtagccttgg cccctaatta tcaggctcca gaaatactgc    2820
tagtttcatt atgccagacc ccatctgaat tctaattctt tgctagaccc cgatagagtc    2880 ccctccccccc aaaaaaaga ttgacaagat gcagtaaatg aaaacagtac ggtgatatgc    2940
tgtattttat tattttgtgt aaaaatagca atacttcaca aaagaatgca tatgcttatg    3000
tataaactat tgtggcgtat ccactgatcc aggcaaaggc ctgaagaaaa gatagacaca    3060
gacagaaagc tggggattgg ctggtctggg ctccctgatg gagaagctgc agcaaccaga    3120
aagctcgtgt gtttattcta aagagctgaa tagggaggcg ggttactcag tacagagaaa    3180
caagaagaca gagtttacag tatacagctg gaccaaggag acaggtgtag ctaatctgag    3240
taggaactct ctctctgtag gggagaattc tctaggctat aaatatgagg gtggagtcaa    3300
aagctttggt ggacattttt tttttttttt aactctgtca cacttggac tcagtattcc      3360 tccaggaaag atttgctatc tttgcttaca tggccctgcc tatgtcatca ataaacattc    3420
gctcagggct tcctctgctc ccaacgctaa tgcttgcaac ttctgcatct ctaaaatgtt    3480
ggtagtgaga ctgcattata gactgcaaat tttaagagac ggccttccac acaggtgggc    3540 cgattttag ttggattatc agttcaaaac attatttaat tgcctcctcc cctctctgtc     3600
tctgactctg tctctctttc ggtggtttgt tttgttttta tagggttg gactatgtag       3660 tttctatata gaacaagttg gccttgaact cacagagagc cacctgcctc tgcctccaaa    3720
tgctgggatt aaagtcctgt gccaccactt cctggcctaa tcctactctt ttatttattt    3780
attttatgtg tatatatgtc tgcttatatg tctgtgtgaa agtgtcagat cccctggaac    3840
tggtgttaca gacagttgtg agctgcaatg tgggtgctgg ggattgaacc tgaatcttct    3900
ggaagagcag ccagtgccct taactgttga gccatccctc cagtcctcct aatcctactc    3960 tgaaatacccc aaagtcactt tggtcttgca ctcctgtaat tccagcacct aggggctgga   4020
ggccagaagt tttggtgttt aaggccaatt ttggttactt agggagttca aggtcagctc    4080
cagttacatg agaagaggga agaaagcagg gagaaggaga gaggttaaga atatgaaaat    4140
gtgagaatct ggaagtaagg ccttgtgtag ccagaacagc tctttacagc tgagctgcat    4200
atccagctct ataaaatcct tttcaaaatc tgagtaagta cggtgagtct gagtgagcac    4260
ggtgcagcag gactatattc ccagtatttta agaagttgtt tggaagagcc cctgttcaaa   4320
accagcctga ctatgtagtg aggaaatcat tttcttttttg ttgttgttgt tctgttttgt   4380
ttgagacagg gtttcttggt gtagtcttgg ctgtcctgga ctctctgtag acagggctgg    4440
tcttcaactc atagagataa cacctacaat gcctcctgag ggctggtgtg tgtgtgtgtg    4500
tgtgtgtgtg tgtgtgtgtg tgtgtgtgtg tgtgtgtgtg tgtgtagata tagtctcaac    4560
aaagtcagtt tttagcactg attttagtaa aaagcatacg gaatctgctg taacatgaag    4620
caggggagga ggagccaaaa tgaagtaagg ttgcactcta aatgccggtt gcacaaaaca    4680
tgcttttaat gaatccctat ataaccagtc ttttcgaagc aaagcacttg aacctttcca    4740
tcctccaggt gtcttctgca gactgaggac acacgaaact gaccttaggt gggggcggg     4800 tggaggggtg gcctgggcca cctcattctt gggagaacag aaatggctct cggtgaggca    4860
ggtggtaagc aggtgcactg gcgacaagga gacgcttcga ccccacccgc gggggaaagg    4920
gaggggatgg gaaaggtggg gagggagtgg gaggggtggg gaggggaggg gaggggaggg    4980
```

```
gaggggaggg gaggggaggg gactgcgggg cctcccaacc ccccgaagcg gaagtggctc    5040
cctgccaaga gctcaggctg tggccagtgt ctaccagaaa tacgtaaaca ttgagtctcc    5100
tgggctaaaa ggtatctaca cttaaacacg agactcacga tttcactttc tggtatagaa    5160
aatcccagcc attatctaac ttaaggatca ccttaagtta ggttacttag aaactaagga    5220
gtcttgtgtg attttctttt ttcttctga tatcttagat agcatcctcc atatggcgtt    5280
tataaagtgt atgctctcat tctttaatat ctaagaaaag acctacattc taggatagct    5340
tcgggaggag tgattcaact tttggatatt tcttttctgc ctttctttct tagcataacc    5400
ataatatgag ctgtacctgg tgacacaggc gtgtcagctg cccgggatgc tgcccgggat    5460
gctgaggcaa gaccatctca agctgggcaa tttagcaaga ccctgtctca aaacacaaag    5520
caaagcaggg tgcgaaaccc acagttgaaa tcgtagcact tagtaagaaa agggctaggc    5580
tatgtgaaac tgcctcaaaa ttcaagggac taaaatattt tttaactgca ctagaataca    5640
gatacaatgc tggcttagca tgtgcaagga cctaggttca gtctccacta tcaaacaaca    5700
acagtaataa cagtaacagt ggcgaaaata aacggctgaa tctcattttt gtttcaagag    5760
caattttgta tcaatttgtg acttaattat atttagaatg ttggattttt ttttaacca    5820 taggcaaaag cttaagacat atttcaatca ggaaaagtac ttttcatcag ctgtggaaat    5880
atagtttctt aaagaaatgc aacactggac atacacacaa acacacctct ataagacagt    5940
ttgcattagg tccatatatt ttaaaaatta gattcactca ttttatttta aaagtgtttc    6000
cttacaggta tgtatgtgca ccatgcccat actttgtact caggaaggtc aggagaaggc    6060
acagttcccc aggaactgaa gttacagaag gttgagggt tttgagccat cacatgggtt    6120
ctgggaattg aacctgggtc ctcggcaaaa gctgctctta actgctgagc catatctcca    6180
gcccttattt ttacataggc tctctctatg tagtcctgac tgttttagaa cttgatatgt    6240
aggccaggct agcctcgaac tcatagagat ccttctgcct ctgcttcctg agtgggttac    6300 cttggaggc cagagacatc aggttcccca gaaaatggga actgaacttg tatgttcagc    6360
aagaccggtt aaataaatgc tcttaagggc tggttcctct ctccagccct tattttatt    6420 cttttttaat tatatgtagg tgtgttatat gtctgcactg tagatttgtg ccaaggaatg    6480
caggtgcctt gggaggccca aggtgttgga tccccaagaa ctgggagctg atcttctgcc    6540
ctctggaaga acagcaagtg ctcttcacca ctgagccatt tctccagccc tgtccttta    6600 ttgttctttt tgttttttg agacaggctt tctctgtgta gccttggctg tcctggatct    6660
ttctctgtag accaggctgg cctcaaattg aactgaaagc atatctctaa tcattagttt    6720
caggattgta cagaatcatt ctgcatactt cttggaaatt acctttttt ttttttaac    6780 tagaatcatc tttgatgctt ttcttttca ctaaatctca ctgtaatttt tccccatttc    6840
tttcagtact ggggattaaa tatcaagact ctctttaagg attagatttt agccttgatt    6900
ctggacctca tataaaactt tcaaaagctc aaccttcagt gttcaggact gaagaagact    6960
agtcgcagtt gctagagtgc ttgcctagca tttgtgaagc gtgggttggg ttcctcagca    7020
ctgtattaac accatgcatg gagatgaatg cctgtatcct cagcacttga gaggtagagg    7080
cgggggaatc agaaatccaa ggttatcctc agttacataa tgagtttgag gtcagcctag    7140
gctatatgag gctctgtctc aagaaaacaa actagccagg tggttgtttg tttgattaaa    7200
ggcacacgcc tttaatccca gcacttggga ggcagagaca ggccgatctc tgtgagttca    7260
aggccagtct ggtctccaga gtaagtgcca ggataggctc caaagctaca cagagaaacc    7320
```

-continued

```
atgtctcgaa aaaccaaaaa aagaaagaaa gaaaacaaac aaacaaatag aacagaacaa    7380
aggccagacc cccaagcttg ggaggcagag tcaagaggag ttctgaggcc agcatagtaa    7440
gttctaggcc agccagggct gcatagtaaa atccctcaga aaacaaacaa gtaacacaca    7500
acaaataggg ctggagagat ggatcaacag ttaagagcac ttggttctct tgcagaggac    7560
agttcagttc ccagcgccca gatcaggcag cacacaacat tctgtagtag ctagctccag    7620
gagacctgac accctgacct ctgaggacac caggcacaca cgttgtgcat agaaacagat    7680
gcaggcaaaa catccacaca tataaaacaa aaaattaaaa ccaataaaac tcctaaactt    7740
ttggtctttc ttgaatcttc aatccctcag gttatgaaat aatcatttat gcagtcaaaa    7800
atttgccatt cttgttgcca ggtgtggtga tgattcgggg aagcagaagc aggcagatct    7860
ctgtgaatga ggccagcctg gtctacaaag tgagtcccag gacagtcagg cctgttacac    7920
agagaaacct tgaaaaaaaa aagataatat gtactgttgt attacccccaa tatataaggc    7980 taaaccatta gaagcacaac actgttaagt acgaaaaata atatctagtg tggtacagtt    8040
actactacta taatacacta atatagctgt gggaaactag ttccaaagat gaattactaa    8100
ccagtgtttc caaggaaata aatgaaagca gagagattag ttctattgct agtgtttcat    8160
tttcgtatat ttcttacaat ttctcttgtt acaaataggc actagggtat caagataatt    8220
ttaacgactg gctgagaacc ctagaaaatc tctgtgaaaa agggatttgt gaaatgagag    8280
agggtaatgt ggccattata gaaaaggctt ttgtgtgcct tgcatgcata gaccctgtgt    8340
ttgatctctt aacaccctcc ttgaccagaa aaagcttctg tggatagaaa atgattagtt    8400
atatatactt ttagggaaac gtagttctgg attctttggt tacaattaac agaattaagt    8460
gcaaacaaag ccagaaacct cctgataaat gagaaaacct gcttgtagaa ggttgtaagg    8520
ctctgtaata taggaattag gagaaaagaa acctgtgtgg tggggcacgt ctgtaatccc    8580
agcattggga agtagaggta gaagattaga atcaaaggc cagcctcagc aacacagtga    8640
gtttgaggcc accctgaact acatcaggtt ctgtctcctt tcttttttt tttttttct    8700 tttcttttt tggtttctct gtgtagtttt ggagcctatc ctggcactag ctctgaagag    8760
caggctggcc tcgaactcag agatcagcca gcctctgctg ggattaaagg tatgcaccac    8820
caacgcccca ggttttgtct caaacaaaca aaaataacat caggaggtgg tgagagggct    8880
cagtggtcac aggcattctc tgcaaagcct gactctgagt tggatccttt agagctacat    8940
ggttgaggga agagaactga ctcctggaag gtgtcctctg gtccccacac atagctatac    9000
acagcatgtg cattcacaca cactaaataa tgctatttt aaaaaaatta aaacaacaa    9060 cagtttgggt tgtgaaaact agaactagat aataggtaag aatcaagtat catgtaaatt    9120
tgctttcaac tcatcccaaa atttgtttta tatttcagtt ttttccttc ctagcttgac    9180 tgtggagtct tgtccggaag caaatagttc ctttgcagat cccacatgtg gacaccggac    9240
agtaggtcct caaatgctcc ttattaggtt ggttcaataa tatcaattgt ttgttactag    9300
gcagtgatgt tgtacatctg gaggagatct cttgagccca taatcaggtt attaggaata    9360
aatactctaa ggctaaaaat gtagcttagt gataagagtg cttgcctggt gtgctgagac    9420
cctcggttcc atctccacaa ccccatattc cattacaaaa tacctttca ccgtccctag    9480 cattaagaaa caaaacaaca aagaagtttt tctttcttct gagatcctgc ccggagaggc    9540
atttaaaact ggccagggcc aaaaaaaaaa aaaaaaag aaaaaaga aagaaaaca    9600 ggctagggcc ggcatggtgg cgcacgcctt taatcccagc acgcaggagg cagaggcagg    9660
gcggatctct gtgagtttga ggtcagcctg gtctacctag tgagtttcag ggcacccagg    9720
```

```
gctaaagaga ctgtctcaaa aacaaaacag ccacacaatc agaaccacag caaaacgcag    9780
ttatgatcct tggaactgta ggaatgacaa gcatttaaat aataggacga gccatttttg    9840
agaagctctg atttcacaag tgtcagggat gggctctggg cgagtaagat tgctaatgct    9900
ggcctctaaa tgagaccacg tggagttgat tagattcttt tcatgttcct cgtgctctat    9960
caaataactg tacccaaata cacacacaca cacacacaca cacaatgcgc gcacacacaa   10020
aatccttttt tagcttaaga agcccagaat cagaagtaaa gctaactgtg ggacttaagt   10080
attattctga acggaactcc cagggcgtga agcgcgcttc aggcttccag agaagcagct   10140
ggcgctggat ggaatgaacc aagaggccag cacaggggga gatccgtcga gctctcggcc   10200
accgagctga gcccttaggt tctggggctg ggaagggtcc ctaggattgt gcacctctcc   10260 cgcggggac aagcagggga tggcggggct gacgtcggga ggtggcctcc acggaaggg    10320 acacccggat ctcgacacag ccttggcagt ggagtcagga agggtaggac agattctgga   10380
cgccctcttg gccagtcctc accgcccac ccccgatgga gccgagagta attcatacaa    10440
aaggagggat cgccttcgcc cctgggaatc ccagggaccg tcgctaaatt ctggccggcc   10500
tcccagcccg gaaccgctgt gcccgccag cgcggcggga ggagcctgcg cctagggcgg    10560
atcgcgggtc ggcgggagag cacaagccca cagtccccgg cggtggggga ggggcgcgct   10620
gagcgggggc ccgggagcca gcgcggggca aactgggaaa gtggtgtcgt gtgctggctc   10680
cgccctcttc ccgagggtgg gggagaacgg tataaaagtg cggtagtcgc gttggacgtt   10740 cttttcgca acgggtttgc cgtcagaacg caggtgagtg gcgggtgtgg cctccgcggg    10800
cccgggctcc ctcctttgag cggggtcgga ccgccgtgcg ggtgtcgtcg gccgggcttc   10860
tctgcgagcg ttcccgccct ggatggcggg ctgtgcggga gggcgagggg gggaggcctg   10920
gcggcggccc cggagcctcg cctcgtgtcg ggcgtgaggc ctagcgtggc ttccgccccg   10980
ccgcgtgcca ccgcggccgc gctttgctgt ctgcccggct gccctcgatt gcctgcccgc   11040
ggcccgggcc aacaaaggga gggcgtggag ctggctggta gggagccccg tagtccgcat   11100
gtcgggcagg gagagcggca gcagtcgggg gggaccgg gccgcccgt cccgcagcac     11160 atgtccgacg ccgcctggac gggtagcggc ctgtgtcctg ataaggcggc cgggcggtgg   11220
gttttagatg ccgggttcag gtggccccgg gtcccggccc ggtctggcca gtaccccgta   11280
gtggcttagc tccgaggagg gcgagcccgc ccgcccggca ccagtgcgt gcgcggaaag    11340 atggccgctc ccgggccctg tagcaaggag ctcaaaatgg aggacgcggc agcccggcgg   11400
agcggggcgg gtgagtcacc cacacaaagg aagagggcct tgcccctcgc cggccgctgc   11460
ttcctgtgac cccgtggtgt accggccgca cttcagtcac cccgggcgct ctttcggagc   11520
accgctggcc tccgctgggg gaggggatct gtctaatggc gttggagttt gctcacattt   11580
ggtgggtgga gactgtagcc aggccagcct ggccatggaa gtaattcttg gaatttgccc   11640
attttgagtt tggagcgaag ctgattgaca aagctgctta gccgttcaaa ggtattcttc   11700
gaactttttt tttaag                                                  11716
```

<210> SEQ ID NO 2
<211> LENGTH: 4057
<212> TYPE: DNA
<213> ORGANISM: Cricetulus griseus

<400> SEQUENCE: 2

```
gtgcatagaa acagatgcag gcaaaacatc cacacatata aaacaaaaaa ttaaaaccaa      60
```

```
taaaactcct aaacttttgg tctttcttga atcttcaatc cctcaggtta tgaaataatc    120
atttatgcag tcaaaaattt gccattcttg ttgccaggtg tggtgatgat tcggggaagc    180
agaagcaggc agatctctgt gaatgaggcc agcctggtct acaaagtgag tcccaggaca    240
gtcaggcctg ttacacagag aaaccttgaa aaaaaaaga taatatgtac tgttgtatta    300
ccccaatata taaggctaaa ccattagaag cacaacactg ttaagtacgg aaaataatat    360
ctagtgtggt acagttacta ctactataat acactaatat agctgtggga aactagttcc    420
aaagatgaat tactaaccag tgtttccaag gaaataaatg aaagcagaga gattagttct    480
attgctagtg tttcattttc gtatatttct tacaatttct cttgttacaa ataggcacta    540
gggtatcaag ataattttaa cgactggctg agaaccctag aaaatctctg tgaaaagggg    600
atttgtgaaa tgagagaggg taatgtggcc attatagaaa aggcttttgt gtgccttgca    660
tgcatagacc ctgtgtttga tctcttaaca ccctccttga ccagaaaaag cttctgtgga    720
tagaaaatga ttagttatat atacttttag ggaaacgtag ttctggattc tttggttaca    780
attaacagaa ttaagtgcaa acaaagccag aaacctcctg ataaatgaga aaacctgctt    840
gtagaaggtt gtaaggctct gtaatatagg aattaggaga aagaaacct gtgtggtggg    900 gcacgtctgt aatcccagca ttgggaagta gaggtagaag attagaaatc aaaggccagc    960
ctcagcaaca cagtgagttt gaggccaccc tgaactacat caggttctgt ctcctttctt    1020
tttttttttt ttttctttc ttttttttggt ttctctgtgt agttttggag cctatcctgg    1080
cactagctct gaagagcagg ctggcctcga actcagagat cagccagcct gctgggat     1140 taaaggtatg caccaccaac gccccaggtt ttgtctcaaa caaacaaaaa taacatcagg    1200
aggtggtgag agggctcagt ggtcacaggc attctctgca aagcctgact ctgagttgga    1260
tcctttagag ctacatggtt gagggaagag aactgactcc tggaaggtgt cctctggtcc    1320
ccacacatag ctatacacag catgtgcatt cacacacact aaataatgct attttttaaaa   1380 aaattaaaaa caacaacagt ttgggttgtg aaaactagaa ctagataata ggtaagaatc    1440
aagtatcatg taaatttgct ttcaactcat cccaaaattt gttttatatt tcagtttttt    1500
tccttcctag cttgactgtg gagtcttgtc cggaagcaaa tagttccttt gcagatccca    1560
catgtggaca ccggacagta ggtcctcaaa tgctccttat taggttggtt caataatatc    1620
aattgtttgt tactaggcag tgatgttgta catctggagg agatctcttg agcccataat    1680
caggttatta ggaataaata ctctaaggct aaaaatgtag cttagtgata agagtgcttg    1740
cctggtgtgc tgagaccctc ggttccatct ccacaacccc atattccatt acaaaatacc    1800
ttttcaccgt ccctagcatt aagaaacaaa acaacaaaga agttttttctt tcttctgaga    1860 tcctgcccgg agaggcattt aaaactggcc agggccaaaa aaaaaaaaaa aaaagaaaa    1920 aaagaaaag aaaacaggct agggccggca tggtggcgca cgcctttaat cccagcacgc    1980
aggaggcaga ggcagggcgg atctctgtga gtttgaggtc agcctggtct acctagtgag    2040
tttcagggca cccagggcta aagagactgt ctcaaaaaca aaacagccac acaatcagaa    2100
ccacagcaaa acgcagttat gatccttgga actgtaggaa tgacaagcat ttaaataata    2160
ggacgagcca ttttttgagaa gctctgattt cacaagtgtc agggatgggc tctgggcgag    2220
taagattgct aatgctggcc tctaaatgag accacgtgga gttgattaga ttcttttcat    2280
gttcctcgtg ctctatcaaa taactgtacc caaatacaca cacacacaca cacacacaca    2340
atgcgcgcac acacaaaatc ctttttttagc ttaagaagcc cagaatcaga agtaaagcta    2400
actgtgggac ttaagtatta ttctgaacgg aactcccagg gcgtgaagcg cgcttcaggc    2460
```

```
ttccagagaa gcagctggcg ctggatggaa tgaaccaaga ggccagcaca ggggcagatc    2520
cgtcgagctc tcggccaccg agctgagccc ttaggttctg gggctgggaa gggtccctag    2580
gattgtgcac ctctcccgcg ggggacaagc agggggatgg cggggctgac gtcgggaggt    2640
ggcctccacg ggaagggaca cccggatctc gacacagcct tggcagtgga gtcaggaagg    2700
gtagggacag attctggacg ccctcttggc cagctcctca ccgccccacc cccgactgga    2760
gccgagagta attcatacaa aaggagggat cgccttcgcc cctgggaatc ccagggaccg    2820
tcgctaaatt ctggccggcc tcccagcccg gaaccgctgt gcccgcccag cgcggcggga    2880
ggagcctgcg cctagggcgg atcgcgggtc ggcgggagag cacaagccca cagtccccgg    2940
cggtggggga ggggcgcgct gagcggggc ccgggagcca gcgcggggca aactgggaaa    3000
gtggtgtcgt gtgctggctc cgccctcttc ccgagggtgg gggagaacgg tataaaagtg    3060
cggtagtcgc gttggacgtt cttttttcgca acgggtttgc cgtcagaacg caggtgagtg    3120
gcgggtgtgg cctccgcggg cccgggctcc ctcctttgag cggggtcggg ccgccgtgcg    3180
ggtgtcgtcg gccgggcttc tctgcgagcg ttcccgccct ggatggcggg ctgtgcggga    3240
gggcgagggg ggaggcctg gcggcggccc cggagcctcg cctcgtgtcg ggcgtgaggc    3300
ctagcgtggc ttccgccccg ccgcgtgcca ccgcggccgc gctttgctgt ctgcccggct    3360
gccctcgatt gcctgcccgc ggccggggcc aacaaaggga gggcgtggag ctggctggta    3420
gggagccccg tagtccgcat gtcgggcagg gagagcggca gcagtcgggg gggggaccgg    3480
gcccgcccgt cccgcagcac atgtccgacg ccgcctggac gggtagcggc ctgtgtcctg    3540
ataaggcggc cgggcggtgg gttttagatg ccgggttcag gtggccccgg gtcccggccc    3600
ggtctggcca gtaccccgta gtggcttagc tccgaggagg gcgaggcccg cccgcccggc    3660
accagttgcg tgcgcggaaa gatggccgct cccgggccct gtagcaagga gctcaaaatg    3720
gaggacgcgg cagcccggcg gagcggggcg ggtgagtcac ccacacaaag gaagagggcc    3780
ttgcccctcg ccggccgctg cttcctgtga ccccgtggtg taccggccgc acttcagtca    3840
ccccgggcgc tctttcggag caccgctggc ctccgctggg ggaggggatc tgtctaatgg    3900
cgttggagtt tgctcacatt tggtgggtgg agactgtagc caggccagcc tggccatgga    3960
agtaattctt ggaatttgcc cattttgagt ttggagcgaa gctgattgac aaagctgctt    4020
agccgttcaa aggtattctt cgaacttttt ttttaag                             4057
```

<210> SEQ ID NO 3
<211> LENGTH: 4180
<212> TYPE: DNA
<213> ORGANISM: Homo sapiens

<400> SEQUENCE: 3

```
tccatttaag tttaatagtg aaagactggt taatgataac aatgcatcgg aaaaccttca     60
ggaggaaagg agaatgtttt gtggaacatt tttgtgtgtg tggcagtttt aagttattag    120
ttttcaaaat cagtactttt taatggaaac aacttgacca aaaatctgtc acagaatttt    180
gagacccatt aaaatacaag tttaatgaga agtctgtctc tgttaatgct gaagtcatta    240
ctaagtgctt agcttagcaa ggtatgtgga tgcccatttg tgttccaagg gattggactg    300
ttcatcagga cccagagctg agtttcaagg gctcaagaga tggcttatta cctgtgggtg    360
tcttgaaggt tctggttggg acaaattagg aatgttttg gcagacatgg tgactacctt    420
catctgggtg agttcagttg atttgtcttg agcctttggg gtttacacaa gtaaatgaca    480
```

-continued

```
tcatacagtt agtgtattgt tagtgaatat taatatatga ggcaggcttt gctctagcaa    540
ttttagaact agttttcagg aaagggttca tcttgtgcat tggatgtttg attctatcac    600
ttagagttta aactgaaagt gctcaagagg ttttatttag gctgggatat aaataagcct    660
ttctgtagct tgtaatggta tcaggaattt aaaaggccat ctggggcaca agattaagc     720
agaaaaggta gaaggtgaga ttgggggact ttgagtactt cacacacttt aatgtgtgag    780
tgctttagtg catatagtac aactgccaga taagggcatc cacatctgat tgtttggaag    840
gcaccttgtg gtttctggga attcagaatt gggagaaaaa tgctcccaac cgctgaagcc    900
cttggtaatc tgcagggtgt ttatttagca ggagataagg acaaaaagtt atagtgtgga    960
gttggttgag ttggtagatg tcattacaac aggtggtctt aaattgggtt aggagtcact   1020
ttgaaatacc tgggccataa gcaaagtggc atttcaccct ttcaggagaa actggtacac   1080
ttatccattc tatagtgcat gcttgttcaa ttgggctgat gactaaaccg gtgactaaag   1140
gtttgtcagt ataaatggat gggttgtagg cagacggtga ggaattacta tacctgcaag   1200
gagtcattgc ctgatctgcc tggaaagggg caggattgag tctcagaacg tgtacaccat   1260
aggatatgga aaaatttgtc acgcctagca ttcaacttag tggtgtagcg ccacctactg   1320
gcactttaaa agcttagcat agaggagcat gtgtgttagg agctcggatg ggatccaggg   1380
cctcaaggtt tgcatgtaaa taaaagccct ttaccaaatt aactacatac cagcatacat   1440
cagtccttta gtgttgaaaa acagaaggga aagctaatat atatagtgct tgctttattt   1500
aagtctagct gattacgtgt ttggttgcca gtgtgactag tctggagttg aatttgtcct   1560
cagacacgta aaatgaatt  tgggattcac aacactctag tatgagggac ctaatggcct   1620
gtaccaggca caaacgtgtc tataaactac acaaaacgaa ggaatttaca ggaattagga   1680
aggtattctt aacattaaaa cattatgggc attttaaaaa aagctttgac aggatttctt   1740
tgtcatggct gtcctggagc tagttgtgta gaccaggctg ggctgaaatc ttgtctgcct   1800
gcctggcttg gacactttt  tattatgtat acaacattct gcttccatgt atatctgcac   1860
attagaagac ggcaccagat ctcctaatgg atggttgtga gccaccatgt ggttgctggg   1920
aattgaactc aggacctctg gaagagcagt gctcttaacc tctgagccat ctccagcccc   1980
agcttgggca cattttaat  ggctgggaaa tcaaaccccc taggccttct gtcagtaatg   2040
aagggctttt ggctaccgag agtaggattt aaggttattc ggagctgcag gtctgcctca   2100
gtgcaggttt gggagtccag catcttagaa aatgcagtga agccaagctg agctatattt   2160
tgtttaaaaa aaaaataagt gggtaaagtg ctgctgagcc tgatgaccaa gctgggacac   2220
aagtagaaga acataggcca atgctctata ttaaaagcat gggtcatttt taatgctctt   2280
gagaaggcta tgcctacact actctcagcc accgcagcgt gtttaaatta aactagtttg   2340
gaaattttct ttggggtaa  gctatttaac ctagtgcctt ggcaggtata ctactgaact   2400
ctcctcctca ttccttttttg ttttttaaga atttcagtca ggctcaggca gcccttaaac   2460
ttgtgattaa gcctgagaac agttacgatt atgagcctat tagtataccg atcaatatgt   2520
gaatttttt  gggatggggg tcaggcctcc ctgcctccca aatactggga ctaaaggctg   2580
caccaccaca acctggctct tgaaatactt ttctacattt tttgggggc  atgggtggga   2640
gagcagggtt tctctgtatt agccctggct ctcctggaac tctgtagacc aggctattct   2700
tgagctcaga ttagcctgtc tctgcctcct aaattctggg attaaggtg  tgtgctactg   2760
ctgcctggct acaagacat  ttttttttt  cttaaattta aaaacaaaag tggttctttt   2820
agaagggtgg ttggtgttgg cacatactcc aagcactcag gttttgagtt tgtcccagga   2880
```

```
atgaagactg cattactgcc gcccctccct ggtaagggct acacagagaa atcctatttg    2940
gagcctatcc tggtaactcg ctctgtagac caggctggcc tcgaactcaa gagaaccacc    3000
tgcctctgaa tgctggtatt aagggcaggc accaccaaca cccagcctaa aaatgtctt     3060 ttttttaaag attttttttt ttttttttac agaataaaca ttctgtttac aatattctgc    3120
ttctatgtat atctgcacac tagaagaggg cacccgatct cataatggat ggttgtgagc    3180
caccaagtgg ttgctgggaa ttgaactcag aacctctgga agagcagtca gtgctcttaa    3240
cctctgagcc atctctccag cccctaaaaa tggctcttga atagggtct caagtagttt     3300 gagactgagt tggctatata acaaggctg gcacatagca ccatgtacag ctgggtttag     3360
tttacatggg gtgttttgt ctctggaggc aggaggatca tttgagcata gggagttaat     3420
agtgaggtca tgttttatct actcttctga attgagaact aagctgatgc aaagcaagtt    3480
tgactgaaga agtccagttt atgagaacaa gggtggaaac taatgtgtca agatggcct     3540 tgcatgtgtt ttagatgatg acccagtcac ttgggaatta ctggatgtgt aagacctata    3600
tcttgacagg agtgaacagt gtcttatagg tcctatatga agaaatgag acatacccat     3660 tttgtttccc ctaagaattc acttttccta acctggttca tgctatttag gttattttac    3720
ttgcaaatcc taggtgctcc cttacccagt attgcttatg tggcaccaaa gtcactcact    3780
cccatgattt gcaagtctct gggaacttcc atgacaacct agaatagcaa ctcaaataca    3840
ttttctcagt accaattttg aagaaaaaat attttgcaaa atagctgtat ggatgggtac    3900
taaatagtga ggttatctcc agaaggccta tgaagaatta aggttgagtt cagttgagtt    3960
cagcagcaag tttaaggttc atccatttt gtacagtgtt ttcctattac ggtaagtgtt     4020
ttgcctgcag gaatatctgt accacatgct tgcctggtac ctatatcggc cagaagaggg    4080
ctttggatcc tctggacttg aattacagat gggtattagc caccatttag gtgctgggaa    4140
ttgaaaccaa gtcctctgga agaacagcaa gtgatcgagt                          4180
```

<210> SEQ ID NO 4
<211> LENGTH: 676
<212> TYPE: DNA
<213> ORGANISM: Homo sapiens

<400> SEQUENCE: 4

```
gttgacattg attattgact agttattaat agtaatcaat tacggggtca ttagttcata     60
gcccatatat ggagttccgc gttacataac ttacggtaaa tggcccgcct ggctgaccgc    120
ccaacgaccc ccgcccattg acgtcaataa tgacgtatgt tcccatagta acgccaatag    180
ggactttcca ttgacgtcaa tgggtggagt atttacggta aactgcccac ttggcagtac    240
atcaagtgta tcatatgcca agtacgcccc ctattgacgt caatgacggt aaatggcccg    300
cctggcatta tgcccagtac atgaccttat gggactttcc tacttggcag tacatctacg    360
tattagtcat cgctattacc atggtgatgc ggttttggca gtacatcaat gggcgtggat    420
agcggtttga ctcacgggga tttccaagtc tccacccat tgacgtcaat gggagtttgt     480
tttggcacca aaatcaacgg gactttccaa aatgtcgtaa caactccgcc ccattgacgc    540
aaatgggcgg taggcgtgta cggtgggagg tctatataag cagagctcgt ttagtgaacc    600
gtcagatcgc ctggagacgc catccacgct gttttgacct ccatagaaga caccgggacc    660
gatccagcct ccggac                                                    676
```

<210> SEQ ID NO 5

```
<211> LENGTH: 173
<212> TYPE: DNA
<213> ORGANISM: Artificial Sequence
<220> FEATURE:
<223> OTHER INFORMATION: Synthetic polynucleotide

<400> SEQUENCE: 5
actctcttcc gcatcgctgt ctgcgagggc cagctgttgg gctcgcggtt gaggacaaac      60
tcttcgcggt ctttccagta ctcttggatc ggaaacccgt cggcctccga acggtactcc     120
gccaccgagg gacctgagcg agtccgcatc gaccggatcg aaaacctct cga             173

<210> SEQ ID NO 6
<211> LENGTH: 3527
<212> TYPE: DNA
<213> ORGANISM: Artificial Sequence
<220> FEATURE:
<223> OTHER INFORMATION: Synthetic polynucleotide

<400> SEQUENCE: 6
gtgcatagaa acagatgcag gcaaaacatc cacacatata aaacaaaaaa ttaaaaccaa      60
taaaactcct aaacttttgg tctttcttga atcttcaatc cctcaggtta tgaaataatc     120
atttatgcag tcaaaaattt gccattcttg ttgccaggtg tggtgatgat tcggggaagc     180
agaagcaggc agatctctgt gaatgaggcc agcctggtct acaaagtgag tcccaggaca     240
gtcaggcctg ttacacagag aaaccttgaa aaaaaaaga taatatgtac tgttgtatta     300
ccccaatata taaggctaaa ccattagaag cacaacactg ttaagtacgg aaaataatat     360
ctagtgtggt acagttacta ctactataat acactaatat agctgtggga aactagttcc     420
aaagatgaat tactaaccag tgtttccaag gaaataaatg aaagcagaga gattagttct     480
attgctagtg tttcattttc gtatatttct tacaatttct cttgttacaa ataggcacta     540
gggtatcaag ataattttaa cgactggctg agaaccctag aaaatctctg tgaaaaaggg     600
atttgtgaaa tgagagaggg taatgtggcc attatagaaa aggcttttgt gtgccttgca     660
tgcatagacc ctgtgtttga tctcttaaca ccctccttga ccagaaaaag cttctgtgga     720
tagaaaatga ttagttatat atacttttag ggaaacgtag ttctggattc tttggttaca     780
attaacagaa ttaagtgcaa acaaagccag aaacctcctg ataaatgaga aaacctgctt     840
gtagaaggtt gtaaggctct gtaatatagg aattaggaga aaagaaacct gtgtggtggg     900
gcacgtctgt aatcccagca ttgggaagta gaggtagaag attagaaatc aaaggccagc     960
ctcagcaaca cagtgagttt gaggccaccc tgaactacat caggttctgt ctcctttctt    1020
tttttttttt ttttctttt tttttttggt ttctctgtgt agttttggag cctatcctgg    1080
cactagctct gaagagcagg ctggcctcga actcagagat cagccagcct tgctgggat    1140 taaaggtatg caccaccaac gccccaggtt ttgtctcaaa caaacaaaaa taacatcagg    1200
aggtggtgag agggctcagt ggtcacaggc attctctgca aagcctgact ctgagttgga    1260
tcctttagag ctacatggtt gagggaagag aactgactcc tggaaggtgt cctctggtcc    1320
ccacacatag ctatacacag catgtgcatt cacacacact aaataatgct attttttaaaa    1380 aaattaaaaa caacaacagt ttgggttgtg aaaactagaa ctagataata ggtaagaatc    1440
aagtatcatg taaatttgct ttcaactcat cccaaaattt gttttatatt tcagttttttt    1500 tccttcctag cttgactgtg gagtcttgtc cggaagcaaa tagttccttt gcagatccca    1560
catgtggaca ccggacagta ggtcctcaaa tgctccttat taggttggtt caataatatc    1620 aattgttttgt tactaggcag tgatgttgta catctggagg agatctcttg agcccataat    1680
```

```
caggttatta ggaataaata ctctaaggct aaaaatgtag cttagtgata agagtgcttg    1740
cctggtgtgc tgagaccctc ggttccatct ccacaacccc atattccatt acaaaatacc    1800
ttttcaccgt ccctagcatt aagaaacaaa acaacaaaga agttttttctt tcttctgaga    1860 tcctgcccgg agaggcattt aaaactggcc agggccaaaa aaaaaaaaaa aaaagaaaa     1920 aaaagaaaag aaaacaggct agggccggca tggtggcgca cgcctttaat cccagcacgc    1980
aggaggcaga ggcagggcgg atctctgtga gtttgaggtc agcctggtct acctagtgag    2040
tttcagggca cccagggcta aagagactgt ctcaaaaaca aaacagccac acaatcagaa    2100
ccacagcaaa acgcagttat gatccttgga actgtaggaa tgacaagcat ttaaataata    2160
ggacgagcca ttttgagaa gctctgattt cacaagtgtc agggatgggc tctgggcgag     2220
taagattgct aatgctggcc tctaaatgag accacgtgga gttgattaga ttcttttcat    2280
gttcctcgtg ctctatcaaa taactgtacc caaatacaca cacacacaca cacacaca      2340 atgcgcgcac acacaaaatc cttttttagc ttaagaagcc cagaatcaga agtaaagcta    2400
actgtgggac ttaagtatta ttctgaacgg aactcccagg gcgtgaagcg cgcttcaggc    2460
ttccagagaa gcagctggcg ctggatgaa tgaaccaaga ggccagcaca ggggcagatc      2520
cgtcgagctc tcggccaccg agctgagccc ttaggttctg gggctgggaa gggtccctag    2580
gattgtgcac ctctcccgcg ggggacaagc aggggatggc ggggctgacg tcggaggtg     2640 gcctccacgg gaagggacac ccggatctcg acacagcctt ggcagtggag tcaggaaggg    2700
taggacagat tctggacgcc ctcttggcca gtcctcaccg ccccacccc gatggagccg      2760 agagtaattc atacaaaagg agggatcgcc ttcgcccctg ggaatcccag ggaccgtcgc    2820
taaattctgg ccggcctccc agcccgggaa cgttgacatt gattattgac tagttattaa    2880
tagtaatcaa ttacggggtc attagttcat agcccatata tggagttccg cgttacataa    2940
cttacggtaa atggcccgcc tggctgaccg cccaacgacc cccgcccatt gacgtcaata    3000
atgacgtatg ttcccatagt aacgccaata gggactttcc attgacgtca atgggtggag    3060
tatttacggt aaactgccca cttggcagta catcaagtgt atcatatgcc aagtacgccc    3120
cctattgacg tcaatgacgg taaatggccc gcctggcatt atgcccagta catgacctta    3180
tgggactttc ctacttggca gtacatctac gtattagtca tcgctattac catggtgatg    3240
cggttttggc agtacatcaa tgggcgtgga tagcggtttg actcacgggg atttccaagt    3300
ctccacccca ttgacgtcaa tgggagtttg ttttggcacc aaaatcaacg ggactttcca    3360
aaatgtcgta acaactccgc cccattgacg caaatgggcg gtaggcgtgt acggtgggag    3420
gtctatataa gcagagctcg tttagtgaac cgtcagatcg cctggagacg ccatccacgc    3480
tgttttgacc tccatagaag acaccgggac cgatccagcc tccggac                   3527
```

<210> SEQ ID NO 7
<211> LENGTH: 3634
<212> TYPE: DNA
<213> ORGANISM: Artificial Sequence
<220> FEATURE:
<223> OTHER INFORMATION: Synthetic polynucleotide

<400> SEQUENCE: 7

```
gtgcatagaa acagatgcag gcaaaacatc cacacatata aaacaaaaaa ttaaaaccaa       60
taaaactcct aaacttttgg tctttcttga atcttcaatc cctcaggtta tgaaataatc      120
atttatgcag tcaaaaattt gccattcttg ttgccaggtg tggtgatgat tcggggaagc      180
```

```
agaagcaggc agatctctgt gaatgaggcc agcctggtct acaaagtgag tcccaggaca    240
gtcaggcctg ttacacagag aaaccttgaa aaaaaaaga taatatgtac tgttgtatta    300
ccccaatata taaggctaaa ccattagaag cacaacactg ttaagtacgg aaaataatat    360
ctagtgtggt acagttacta ctactataat acactaatat agctgtggga aactagttcc    420
aaagatgaat tactaaccag tgtttccaag gaaataaatg aaagcagaga gattagttct    480
attgctagtg tttcattttc gtatatttct tacaatttct cttgttacaa ataggcacta    540
gggtatcaag ataattttaa cgactggctg agaaccctag aaaatctctg tgaaaaaggg    600
atttgtgaaa tgagagaggg taatgtggcc attatagaaa aggcttttgt gtgccttgca    660
tgcatagacc ctgtgtttga tctcttaaca ccctccttga ccagaaaaag cttctgtgga    720
tagaaaatga ttagttatat atacttttag ggaaacgtag ttctggattc tttggttaca    780
attaacagaa ttaagtgcaa acaaagccag aaacctcctg ataaatgaga aaacctgctt    840
gtagaaggtt gtaaggctct gtaatatagg aattaggaga aaagaaacct gtgtggtggg    900
gcacgtctgt aatcccagca ttgggaagta gaggtagaag attagaaatc aaaggccagc    960
ctcagcaaca cagtgagttt gaggccaccc tgaactacat caggttctgt ctcctttctt   1020
tttttttttt ttttctttc tttttttggt ttctctgtgt agttttggag cctatcctgg   1080
cactagctct gaagagcagg ctggcctcga actcagagat cagccagcct gctgggat    1140 taaaggtatg caccaccaac gcccaggtt ttgtctcaaa caaacaaaaa taacatcagg   1200
aggtggtgag agggctcagt ggtcacaggc attctctgca aagcctgact ctgagttgga   1260
tcctttagag ctacatggtt gagggaagag aactgactcc tggaaggtgt cctctggtcc   1320
ccacacatag ctatacacag catgtgcatt cacacacact aaataatgct attttttaaaa  1380 aaattaaaaa caacaacagt ttgggttgtg aaaactagaa ctagataata ggtaagaatc   1440
aagtatcatg taaatttgct ttcaactcat cccaaaattt gttttatatt tcagtttttt   1500
tccttcctag cttgactgtg gagtcttgtc cggaagcaaa tagttccttt gcagatccca   1560
catgtggaca ccggacagta ggtcctcaaa tgctccttat taggttggtt caataatatc   1620
aattgtttgt tactaggcag tgatgttgta catctggagg agatctcttg agcccataat   1680
caggttatta ggaataaata ctctaaggct aaaaatgtag cttagtgata agagtgcttg   1740
cctggtgtgc tgagaccctc ggttccatct ccacaacccc atattccatt acaaaatacc   1800
ttttcaccgt ccctagcatt aagaaacaaa acaacaaaga agttttctt tcttctgaga   1860 tcctgcccgg agaggcattt aaaactggcc agggccaaaa aaaaaaaaa aaaagaaaa    1920 aaagaaaag aaaacaggct agggccggca tggtggcgca cgcctttaat cccagcacgc   1980
aggaggcaga ggcagggcgg atctctgtga gtttgaggtc agcctggtct acctagtgag   2040
tttcagggca cccagggcta aagagactgt ctcaaaaaca aaacagccac acaatcagaa   2100
ccacagcaaa acgcagttat gatccttgga actgtaggaa tgacaagcat ttaaataata   2160
ggacgagcca ttttgagaa gctctgattt cacaagtgtc agggatgggc tctgggcgag   2220
taagattgct aatgctggcc tctaaatgag accacgtgga gttgattaga ttcttttcat   2280
gttcctcgtg ctctatcaaa taactgtacc caaatacaca cacacacaca cacacacaca  2340
atgcgcgcac acacaaaatc cttttttagc ttaagaagcc cagaatcaga agtaaagcta   2400
actgtgggac ttaagtatta ttctgaacgg aactcccagg gcgtgaagcg cgcttcaggc   2460
ttccagagaa gcagctggcg ctggatggaa tgaaccaaga ggccagcaca ggggcagatc   2520
cgtcgagctc tcggccaccg agctgagccc ttaggttctg gggctgggaa gggtccctag   2580
```

-continued

```
gattgtgcac ctctcccgcg ggggacaagc aggggatggc ggggctgacg tcgggaggtg    2640
gcctccacgg gaagggacac ccggatctcg acacagcctt ggcagtggag tcaggaaggg    2700
taggacagat tctggacgcc ctcttggcca gtcctcaccg ccccaccccc gatggagccg    2760
agagtaattc atacaaaagg agggatcgcc ttcgccctg  ggaatcccag ggaccgtcgc    2820
taaattctgg ccggcctccg cggccgcgaa cgttgacatt gattattgac tagttattaa    2880
tagtaatcaa ttacggggtc attagttcat agcccatata tggagttccg cgttacataa    2940
cttacggtaa atggcccgcc tggctgaccg cccaacgacc cccgcccatt gacgtcaata    3000
atgacgtatg ttcccatagt aacgccaata gggactttcc attgacgtca atgggtggag    3060
tatttacggt aaactgccca cttggcagta catcaagtgt atcatatgcc aagtacgccc    3120
cctattgacg tcaatgacgg taaatggccc gcctggcatt atgcccagta catgacctta    3180
tgggactttc ctacttggca gtacatctac gtattagtca tcgctattac catggtgatg    3240
cggttttggc agtacatcaa tgggcgtgga tagcggtttg actcacgggg atttccaagt    3300
ctccacccca ttgacgtcaa tgggagtttg ttttggcacc aaaatcaacg ggactttcca    3360
aaatgtcgta acaactccgc cccattgacg caaatgggcg gtaggcgtgt acggtgggag    3420
gtctatataa gcagagctcg tttagtgaac cgtcatgatc actctcttcc gcatcgctgt    3480
ctgcgagggc cagctgttgg gctcgcggtt gaggacaaac tcttcgcggt ctttccagta    3540
ctcttggatc ggaaacccgt cggcctccga acggtactcc gccaccgagg gacctgagcg    3600
agtccgcatc gaccggatcg gaaaacctct cgaa                                3634
```

US 9,297,024 B2

RECOMBINANT PROTEIN EXPRESSION USING A HYBRID CHEF1 PROMOTER

CROSS-REFERENCE TO RELATED APPLICATION

This application claims the benefit of priority of U.S. Provisional Patent Application Ser. No. 61/777,603, filed Mar. 12, 2013. The disclosure of the priority application is incorporated herein by reference.

This application contains, as a separate part of the disclosure, a sequence listing in computer-readable form (Filename: 44744A_SeqListing.txt; Size: 37,528 bytes; Created: Mar. 11, 2014) which is incorporated by reference in its entirety.

FIELD OF THE INVENTION

This invention is directed to expression vectors comprising a novel promoter-enhancer combination that increases heterologous protein expression and has practical application in the field of recombinant protein production.

BACKGROUND OF THE INVENTION

Increasing recombinant protein expression through improvements in transcription, translation, protein folding and/or secretion is a fundamental priority for optimizing yield during cell line development. The Chinese hamster ovary elongation factor 1-α (CHEF1) expression system has been used extensively to create clinical cell lines for producing recombinant proteins. The elongation factor 1-α (EF-1α) gene is highly expressed in most tissue types, and EF-1 is one of the most abundant proteins in human cells (Beck et al., *Molecular Systems Biology* 7: 549; 2011). CHEF1 expression vectors achieve high-level recombinant protein expression in Chinese hamster ovary (CHO) cells, as well as in non-hamster cells.

CHEF1 expression is coordinated with growth such that titer increases are driven by increased volumetric productivity. Typically, protein expression initiates early in the exponential phase of growth and drops off during stationary phase and decline. The linkage between protein expression and cell growth is consistent with the regulation of the native EF-1α gene, which is constitutively expressed to function in ribosomal protein complexes. Expression of EF-1α has been documented to increase in transformed (Sanders et al., *Nucleic Acids Research* 20: 5907; 1992) and mitogen-stimulated cells (Thomas and Thomas, *Journal of Cell Biology* 103: 2137; 1986), consistent with constitutive expression of EF-1α in actively growing cells. In addition to transcriptional control in growing cells, the growth factor insulin regulates the translation of EF-1α through the mRNA 5' untranslated region (5'UTR) (Hammond and Bowman, *Journal of Biological Chemistry* 25: 17785; 1988; Proud and Denton, *Biochemical Journal* 328: 329; 1997). This translational control is achieved through the Tract of Polypyrimidine (TOP) sequence found in the 5'UTR (Mariottini and Amaldi, *Molecular and Cellular Biology* 10: 816; 1990).

CHEF1 expression systems have been shown to be capable of achieving higher levels of protein expression than vectors employing other commonly used promoters, such as the cytomegalovirus (CMV), human EF-1α, and Simian virus 40 (SV40) promoters (Running Deer and Allison, *Biotechnology Progress* 20: 880; 2004). The CMV promoter is one of the most widely used promoters for recombinant protein expression. For example, the glutamine synthetase (GS) system uses a murine or human CMV promoter (Kalwy, S., "Towards stronger gene expression—a promoter's tale," 19th European Society for Animal Cell Technology (ESACT) meeting, 2005). The commercial expression plasmid pcDNA™3 (Life Technologies Corp., Carlsbad, Calif.) carries a CMV promoter derived from the major immediate-early (IE) gene (GenBank Accession # K03104.1) described previously (Boshart et al., *Cell* 1985; 4:521). Another commonly used CMV promoter is derived from the human CMV strain AD169 (GenBank Accession # X17403.1), also known as human herpesvirus 5.

Vectors containing CHEF1 regulatory DNA result in improved expression of recombinant proteins that is up to 280-fold greater than from CMV-controlled plasmids (Running Deer and Allison, 2004). Increased expression of a variety of proteins of interest, including secreted and membrane-bound proteins, has been achieved in different eukaryotic cell lines, including non-hamster cells, using CHEF1-driven vectors. Transfection efficiencies between CHEF1 and CMV vectors are comparable, but expression levels in clones transfected with CHEF 1 vectors are generally uniformly higher.

Despite the demonstrated success of CHEF1 vectors in driving high-level expression of recombinant proteins, there exists an ongoing need to develop improved expression systems.

SUMMARY OF THE INVENTION

The disclosure provides an expression vector for high-level expression of recombinant proteins. In various aspects, the expression vector comprises CHEF1 transcriptional regulatory DNA elements and a CMV promoter and/or a human adenovirus tripartite leader (AdTPL) sequence.

In various aspects, an expression vector according to the disclosure comprises 5' CHEF1 transcriptional regulatory DNA. In various embodiments, the 5' CHEF1 transcriptional regulatory DNA comprises SEQ ID NO: 1. In various embodiments, the 5' CHEF1 transcriptional regulatory DNA comprises DNA located between position 1 and position 11,716 in SEQ ID NO: 1. In various aspects, the 5' CHEF1 transcriptional regulatory DNA comprises DNA located between position 10,744 and 11,716 in SEQ ID NO: 1. In various embodiments, the 5' CHEF1 transcriptional regulatory DNA comprises SEQ ID NO: 2. In various embodiments, the 5' CHEF1 transcriptional regulatory DNA comprises DNA located between position 1 and position 4057 in SEQ ID NO: 2.

In various aspects, an expression vector according to the disclosure further comprises 3' CHEF1 transcriptional regulatory DNA. In various embodiments, the 3' CHEF1 transcriptional regulatory DNA comprises SEQ ID NO: 3. In various embodiments, the 3' CHEF1 transcriptional regulatory DNA comprises DNA located between position 1 and position 4180 in SEQ ID NO: 3. In various aspects, the 3' CHEF1 transcriptional regulatory DNA comprises DNA located between position 1 and position 209 in SEQ ID NO: 3. In various embodiments, 3' CHEF1 transcriptional regulatory DNA comprises about 4.2 kilobases.

In various embodiments, an expression vector according to the disclosure comprises CHEF1 transcriptional regulatory DNA and a CMV promoter. In various embodiments, the expression vector comprises CHEF1 transcriptional regulatory DNA and an AdTPL sequence. In various aspects, the expression vector comprises CHEF1 transcriptional regulatory DNA, a CMV promoter, and an AdTPL sequence.

In various aspects, in an expression vector according to the disclosure, a CMV promoter and/or an AdTPL sequence is inserted into 5' CHEF1 transcriptional regulatory DNA. In various embodiments, in an expression vector comprising DNA set out in SEQ ID NO: 1, one or more bases between position 1 and position 11,716 in SEQ ID NO: 1 is/are deleted and replaced with a CMV promoter and/or an AdTPL sequence. In various aspects, one or more bases between position 10,512 and position 11,716 in SEQ ID NO: 1 is/are deleted and replaced with a CMV promoter and/or AdTPL sequence. In various aspects, an expression vector according to the disclosure comprises one or more of the polynucleotides set forth in SEQ ID NO: 4, SEQ ID NO: 5, SEQ ID NO: 6 and SEQ ID NO: 7.

In various embodiments, an expression vector according to the disclosure further comprises a selectable marker gene. In various embodiments, an expression vector according to the disclosure further comprises a polynucleotide encoding a protein of interest that is operably linked to the 5' CHEF1 transcriptional regulatory DNA, the 3' CHEF1 transcriptional regulatory DNA, the CMV promoter, and/or the AdTPL sequence.

The disclosure also provides host cells transformed, transduced, or transfected with an expression vector comprising CHEF1 transcriptional regulatory DNA and a CMV promoter and/or an AdTPL sequence. In various aspects, the host cell is a prokaryotic or eukaryotic cell. In various aspects, the host cell is a hamster cell, and in various embodiments, the host cell is a Chinese hamster ovary (CHO) cell. In various aspects, the host cell is a non-hamster mammalian cell. In various embodiments, the host cell is a human cell. The expression vector of the disclosure comprising CHEF1 transcriptional regulatory DNA in combination with a CMV promoter and/or an AdTPL sequence achieves a synergistic increase in the protein expression capacity of the host cells.

BRIEF DESCRIPTION OF THE DRAWINGS

FIG. 4 shows the viability and productivity of CHO host cells transfected with the vector pDEF38-GP1, pDEF85-GP1, or pDEF86-GP1. Replicate transfection pools were run in 12-day fed-batch production models and fed Feed C on Days 3, 5, and 7 and CB on Days 0, 3, 5, and 7 in CD-CIM1 base media. Productions were run at 37° C. and shifted to 34° C. on Day 3. Viable cell density, percent viability, and productivity were measured on Days 3, 5, 7, 10, and 12. FIG. 4A shows viable cell density, with days shown on the x-axis and viable cell density, measured in 10e5 cells per milliliter, depicted on the y-axis. FIG. 4B shows percent viability, with days shown on the x-axis and percent cell viability depicted on the y-axis.

FIG. 7 shows the growth and productivity of CHO host cells transfected with the vector pDEF38-MAb1, pDEF85-MAb1, or pDEF86-MAb1 grown in BF1-supplemented media. Replicate transfection pools were run in 12-day fed-batch production models and fed BF1 in CD-CIM1 base media plus CB on Days 4, 6, 8, 10, and 12. Productions were run at 37° C. and shifted to 32.5° C. on Day 5. Antibody titer samples were measured on Days 7, 10, 12 and 14. FIG. 7A shows growth, with days shown on the x-axis and viable cell density, measured in 10e5 cells per milliliter, depicted on the y-axis. FIG. 7B shows productivity, with days shown on the x-axis and protein titer, measured in micrograms per milliliter, depicted on the y-axis.

FIG. 8 shows the growth and productivity of CHO host cells transfected with the vector pDEF38-MAb1 or pDEF85-MAb1. Twelve randomly selected clones expressing MAb1 after transfection with pDEF38 or pDEF85 were run in 12-day fed-batch production models and fed BF1 in CD-CIM1 base media plus CB on Days 4, 6, 8, 10, and 12. Productions were run at 37° C. and shifted to 32.5° C. on Day 5. Viable cell density and antibody titer were measured on Days 4, 6, 11 and 13. FIG. 8A shows the growth of each clone, with days shown on the x-axis and viable cell density, measured in 10e5 cells per milliliter, depicted on the y-axis. FIG. 8B shows the productivity of each clone, with days shown on the x-axis and the antibody titer, measured in micrograms per milliliter, depicted on the y-axis.

FIG. 9 shows the productivity of CHO host cells transfected with the vector pDEF38-GP1 or pDEF85-GP1. Eight clones expressing GP1 after transfection with pDEF38-GP1 or pDEF85-GP1 were selected using flow cytometry and run in 12-day fed-batch production model. The clones were fed BF1 in CD-CIM1 base media plus CB on Days 4, 6, 8, 10, and 12. Productions were run at 37° C. and shifted to 32.5° C. on Day 3. Titers were measured on Days 5, 7, 10, 12 and 14. FIG. 9A shows the productivity of clones transfected with the CHEF1 vector pDEF38-GP1, with days shown on the x-axis and the protein titer, measured in micrograms per milliliter, depicted on the y-axis. FIG. 9B shows the productivity of clones transfected with the CHEF1-CMV vector pDEF85-GP1, with days shown on the x-axis and the protein titer, measured in micrograms per milliliter, depicted on the y-axis.

DETAILED DESCRIPTION OF THE INVENTION

Figure 1:
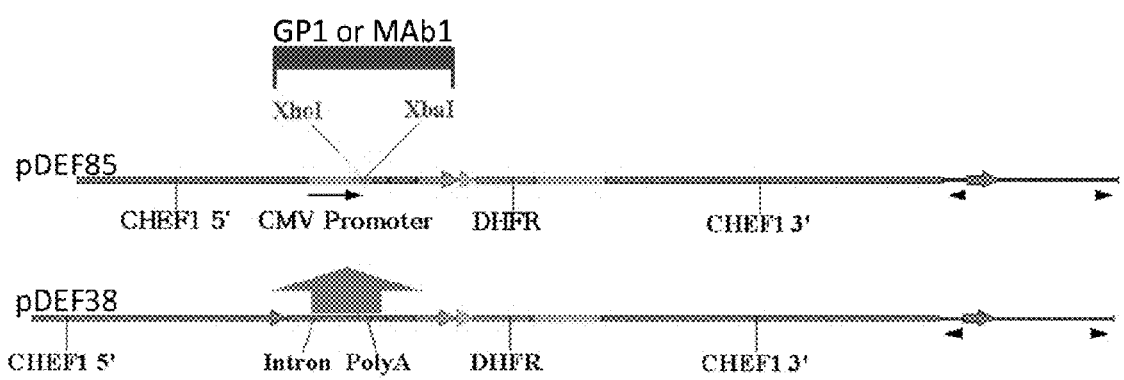
FIG. 1 shows a map of the expression vector pDEF85 comprising 5' and 3' CHEF1 transcriptional regulatory DNA and a CMV promoter. The CMV promoter replaces 1217 nucleotides (from position 2866 to position 4083) of the 5' CHEF1 DNA in vector pDEF38 to create pDEF85. GP1 and MAb1 reporter genes were cloned into the XhoI-XbaI cloning sites to make the expression vectors pDEF85-GP1 and pDEF85-MAb1.

The present disclosure provides an expression vector comprising a combination of regulatory DNA elements for achieving high-level protein expression and improved productivity compared to vectors known in the field The disclosure also provides a host cell transformed with an expression vector described herein. The expression vector of the disclosure comprises CHEF1 transcriptional regulatory DNA combined with a CMV promoter and/or an AdTPL sequence. The use of CHEF1 transcriptional regulatory DNA elements in an expression vector to achieve high-level expression of recombinant proteins has been previously described (U.S. Pat. No. 5,888,809; Running Deer and Allison, 2004). Protein expression from CHEF1-driven vectors has been shown to be significantly higher than from CMV promoter-controlled vectors for a number of different protein and host cell types, and the increase can be greater than 250-fold (Running Deer and Allison, 2004). The AdTPL sequence is a 200-nucleotide 5' noncoding sequence found on late viral mRNAs that enhances their translation (Logan, *PNAS* 81: 3655; 1984).

Considering the improved protein expression obtained using CHEF1-controlled vectors, the addition of non-CHEF1 control regions, such as a CMV promoter or an AdTPL sequence, to a CHEF1 expression vector would be counterintuitive. The presence of such non-CHEF1 control regions could disrupt the cooperative action of individual CHEF1 transcriptional regulatory elements and would not be expected to act in concert with the CHEF1 regulatory DNA to yield improved protein expression. However, the expression vector of the present disclosure, which comprises CHEF1 transcriptional regulatory DNA and a CMV promoter and/or an AdTPL sequence, surprisingly yields increased protein expression compared to vectors comprising only CHEF1 control regions.

As used herein, the following definitions may be useful in aiding the skilled practitioner in understanding the disclosure:

The term "expression vector" refers to any molecule used to transfer coding information to a host cell. In various aspects, the expression vector is a nucleic acid, a plasmid, a cosmid, a virus, or an artificial chromosome.

The term "host cell" refers to a cell that has been transformed, transfected, or transduced by an expression vector bearing a gene of interest, which is then expressed by the cell. A host cell is, in various aspects, a prokaryotic or eukaryotic cell. In various aspects, the host cell is a bacteria cell, a protist cell, a fungal cell, a plant cell, or an animal cell. The term also refers to progeny of the parent host cell, regardless of whether the progeny is identical in genotype or phenotype to the parent, as long as the gene of interest is present.

The term "CMV promoter" refers to CMV promoter sequences known in the art. In various aspects, the CMV promoter is of any origin, including murine (mCMV) or human (hCMV). In various aspects, a hCMV is derived from any CMV strain. In various aspects, the CMV strain is AD169, Davis, Toledo, or Towne. In various embodiments of the disclosure, the CMV promoter contains the polynucleotide set forth in SEQ ID NO: 4.

The term "AdTPL sequence" refers to the approximately 200 nucleotide, 5' noncoding sequence present in human adenovirus late viral mRNAs that is known in the art. In various embodiments, the AdTPL sequence contains the polynucleotide set forth in SEQ ID NO: 5.

The term "CHEF1 transcriptional regulatory DNA" refers to noncoding sequences containing cis-acting regulatory elements capable of controlling transcription of the CHEF1 gene, such as the promoter region and elements such as enhancers, insulators, and scaffold/matrix attachment regions.

The term "5' CHEF1 transcriptional regulatory DNA" refers to DNA, when in nature, located 5', i.e., upstream, of the start codon in the CHEF1 gene in the Chinese hamster genome.

The term "3' CHEF1 transcriptional regulatory DNA" refers to DNA, when in nature, located 3', i.e., downstream, of the stop codon in the CHEF1 gene in the Chinese hamster genome.

The terms "approximately" and "about" refer to quantities that are within close range of a reference amount. With respect to polynucleotides, a sequence that is approximately/about a specified length is within 5% of the recited length.

In various aspects, an expression vector according to the disclosure comprises CHEF1 transcriptional regulatory DNA and a CMV promoter and/or an AdTPL sequence. In various aspects, the CHEF1 transcriptional regulatory DNA comprises 5' CHEF1 transcriptional regulatory DNA and/or 3' CHEF1 transcriptional regulatory DNA.

In various embodiments, the 5' CHEF1 transcriptional regulatory DNA comprises the polynucleotide set forth in SEQ ID NO: 1. The disclosure also provides 5' CHEF1 transcriptional regulatory DNA that is at least 99%, at least 98%, at least 97%, at least 96%, at least 95%, at least 94%, at least 93%, at least 92%, at least 91%, at least 90%, at least 85%, at least 80%, at least 75% or at least 70% identical to the polynucleotide set out in SEQ ID NO: 1. In various embodiments, the 5' CHEF1 transcriptional regulatory DNA comprises DNA located between position 1 and position 11,716 of SEQ ID NO: 1, i.e., a portion of SEQ ID NO: 1. The disclosure also provides 5' CHEF1 transcriptional regulatory DNA that is at least 99%, at least 98%, at least 97%, at least 96%, at least 95%, at least 94%, at least 93%, at least 92%, at least 91%, at least 90%, at least 85%, at least 80%, at least 75% or at least 70% identical to DNA located between position 1 and position 11,716 in SEQ ID NO: 1. In various aspects, the 5' CHEF1 transcriptional regulatory DNA comprises DNA located between position 10,744 and position 11,716 in SEQ ID NO: 1. The disclosure also provides 5' CHEF1 transcriptional regulatory DNA that is at least 99%, at least 98%, at least 97%, at least 96%, at least 95%, at least 94%, at least 93%, at least 92%, at least 91%, at least 90%, at least 85%, at least 80%, at least 75% or at least 70% identical to DNA located between position 10,744 and position 11,716 in SEQ ID NO: 1. In various embodiments, the 5' CHEF1 transcriptional regulatory DNA comprises the polynucleotide set forth in SEQ ID NO: 2. The disclosure also provides 5' CHEF1 transcriptional regulatory DNA that is at least 99%, at least 98%, at least 97%, at least 96%, at least 95%, at least 94%, at least 93%, at least 92%, at least 91%, at least 90%, at least 85%, at least 80%, at least 75% or at least 70% identical to the polynucleotide set out in SEQ ID NO; 2. In various embodiments, the 5' CHEF1 transcriptional regulatory DNA comprises DNA located between position 1 and position 4057 of SEQ ID NO: 2, i.e., a portion of SEQ ID NO: 2. The disclosure also provides 5' CHEF1 transcriptional regulatory DNA that is at least 99%, at least 98%, at least 97%, at least 96%, at least 95%, at least 94%, at least 93%, at least 92%, at least 91%, at least 90%, at least 85%, at least 80%, at least 75% or at least 70% identical to DNA located between position 1 and position 4057 of SEQ ID NO: 2.

In various aspects, the expression vector according to the disclosure further comprises 3' CHEF1 transcriptional regulatory DNA. In various embodiments, the 3' CHEF1 transcriptional regulatory DNA comprises the polynucleotide set forth in SEQ ID NO: 3. The disclosure also provides 3' CHEF1 transcriptional regulatory DNA that is at least 99%, at least 98%, at least 97%, at least 96%, at least 95%, at least 94%, at least 93%, at least 92%, at least 91%, at least 90%, at least 85%, at least 80%, at least 75% or at least 70% identical to the polynucleotide set out in SEQ ID NO: 3. In various embodiments, the 3' CHEF1 transcriptional regulatory DNA comprises DNA located between position 1 and position 4180 in SEQ ID NO: 3, i.e., a portion of SEQ ID NO: 3. The disclosure also provides 3' CHEF1 transcriptional regulatory DNA that is at least 99%, at least 98%, at least 97%, at least 96%, at least 95%, at least 94%, at least 93%, at least 92%, at least 91%, at least 90%, at least 85%, at least 80%, at least 75% or at least 70% identical to DNA located between position 1 and position 4180 in SEQ ID NO: 3, i.e., a portion of SEQ ID NO: 3. In various aspects, the 3' CHEF1 transcriptional regulatory DNA comprises DNA located between position 1 and position 209 in SEQ ID NO: 3. The disclosure also provides 3' CHEF transcriptional regulatory DNA that is at least 99%, at least 98%, at least 97%, at least 96%, at least 95%, at least 94%, at least 93%, at least 92%, at least 91%, at least 90%, at least 85%, at least 80%, at least 75% or at least 70% identical to DNA located between position 1 and position 209 in SEQ ID NO: 3. In various embodiments, the 3' CHEF1 transcriptional regulatory DNA may comprise about 4.2 kilobases.

In various embodiments, the expression vector according to the disclosure comprises CHEF1 transcriptional regulatory DNA elements and a CMV promoter. In various aspects, the CMV promoter comprises the polynucleotide set forth in SEQ ID NO: 4. The disclosure also provides a CMV promoter that is at least 99%, at least 98%, at least 97%, at least 96%, at least 95%, at least 94%, at least 93%, at least 92%, at least 91%, at least 90%, at least 85%, at least 80%, at least 75% or at least 70% identical to the polynucleotide set forth in SEQ ID NO: 4. In various aspects, the expression vector comprising 5' CHEF1 transcriptional regulatory DNA and a CMV promoter comprises the polynucleotide set forth in SEQ ID NO: 6. The disclosure also provides 5' CHEF1 transcriptional regulatory DNA and a CMV promoter that is at least 99%, at least 98%, at least 97%, at least 96%, at least 95%, at least 94%, at least 93%, at least 92%, at least 91%, at least 90%, at least 85%, at least 80%, at least 75% or at least 70% identical to the polynucleotide set forth in SEQ ID NO: 6. In various embodiments, the expression vector comprises CHEF1 transcriptional regulatory DNA and an AdTPL sequence. In various aspects, the AdTPL sequence comprises the polynucleotide set forth in SEQ ID NO: 5. The disclosure also provides an AdTPL sequence that is at least 99%, at least 98%, at least 97%, at least 96%, at least 95%, at least 94%, at least 93%, at least 92%, at least 91%, at least 90%, at least 85%, at least 80%, at least 75% or at least 70% identical to the polynucleotide set forth in SEQ ID NO: 5. In various embodiments, the expression vector comprises CHEF1 transcriptional regulatory DNA, a CMV promoter and an AdTPL sequence. In various aspects, the expression vector comprising 5' CHEF1 transcriptional regulatory DNA, a CMV promoter, and an AdTPL sequence comprises the polynucleotide set forth in SEQ ID NO: 7. The disclosure also provides 5' CHEF1 transcriptional regulatory DNA, a CMV promoter, and an AdTPL sequence that is at least 99%, at least 98%, at least 97%, at least 96%, at least 95%, at least 94%, at least 93%, at least 92%, at least 91%, at least 90%, at least 85%, at least 80%, at least 75% or at least 70% identical to the polynucleotide set forth in SEQ ID NO: 7.

In various embodiments, a CMV promoter and/or an AdTPL sequence is inserted into the 5' CHEF1 transcriptional regulatory DNA in an expression plasmid according to the disclosure. In various embodiments, in an expression vector comprising DNA set out in SEQ ID NO: 1, one or more bases between position 1 and position 11,716 of SEQ ID NO: 1 is/are deleted and replaced with a CMV promoter and/or AdTPL sequence. In various embodiments, the proximal 5' CHEF1 promoter region is replaced with a CMV promoter and/or an AdTPL sequence. For example and without limitation, in various aspects, one or more bases between position 10,512 and position 11,716 of SEQ ID NO: 1 is/are deleted and replaced with a CMV promoter, an AdTPL sequence, or a CMV promoter and an AdTPL sequence.

The expression vector according to the disclosure further comprises a polynucleotide encoding a protein of interest. In various aspects, the polynucleotide is operably linked to the 5' CHEF1 transcriptional regulatory DNA, the 3' CHEF1 transcriptional regulatory DNA, the CMV promoter, and/or the AdTPL sequence. The expression vector is useful for any protein and is expected to provide higher protein expression than CHEF1 or CMV alone. In various aspects, the expression vector further comprises a selectable marker gene for identification of transformed cells. Examples of suitable selectable marker genes include, but are not limited to, neomycin phosphotransferase (npt II), hygromycin phosphotransferase (hpt), dihydrofolate reductase (dhfr), zeocin, phleomycin, bleomycin resistance gene (ble), gentamycin acetyltransferase, streptomycin phosphotransferase, mutant form of acetolactate synthase (als), bromoxynil nitrilase, phosphinothricin acetyl transferase (bar), enolpyruvylshikimate-3-phosphate (EPSP) synthase (aro A), muscle specific tyrosine kinase receptor molecule (MuSK-R), copper-zinc superoxide dismutase (sod1), metallothioneins (cup1, MT1), beta-lactamase (BLA), puromycin N-acetyl-transferase (pac), blasticidin acetyl transferase (Ns), blasticidin deaminase (bsr), histidinol dehydrogenase (HDH), N-succinyl-5-aminoimidazole-4-carboxamide ribotide (SAICAR) synthetase (ade1), argininosuccinate lyase (arg4), beta-isopropylmalate dehydrogenase (leu2), invertase (suc2), orotidine-5'-phosphate (OMP) decarboxylase (ura3), and orthologs of any of the foregoing.

The disclosure also provides host cells transformed, transduced, or transfected with an expression vector comprising CHEF1 transcriptional regulatory DNA and a CMV promoter and/or an AdTPL sequence. In various aspects, the host cell is a prokaryotic or eukaryotic cell. In various aspects, the host cell is a hamster cell. In various aspects, the hamster cell is a CHO cell. In various embodiments, the host cell is a non-hamster mammalian cell, and in various aspects, the cell is a human cell.

Embodiments contemplated in view of the foregoing description include, but are not limited to, the following numbered embodiments:

1. An expression vector comprising Chinese Hamster Elongation Factor-1α (CHEF1) transcriptional regulatory DNA and a cytomegalovirus (CMV) promoter and/or an adenovirus tripartite leader (AdTPL) sequence.

2. The expression vector of embodiment 1, wherein the CHEF1 transcriptional regulatory DNA comprises 5' CHEF transcriptional regulatory DNA.

3. The expression vector of embodiment 2, wherein the 5' CHEF1 transcriptional regulatory DNA comprises Sequence ID NO: 1 or a polynucleotide at least 95% identical to Sequence ID NO: 1.

4. The expression vector of embodiment 2, wherein the 5' CHEF1 transcriptional regulatory DNA comprises DNA located between position 1 and position 11,716 in Sequence ID NO: 1 or a polynucleotide at least 95% identical to DNA located between position 1 and position 11,716 in Sequence ID NO: 1.

5. The expression vector of embodiment 4, wherein the 5' CHEF1 transcriptional regulatory DNA comprises DNA located between position 10,774 and position 11,716 in Sequence ID NO: 1 or a polynucleotide at least 95% identical to DNA located between position 10,774 and position 11,716 in Sequence ID NO: 1.

6. The expression vector of embodiment 2, wherein the 5' CHEF1 transcriptional regulatory DNA comprises Sequence ID NO: 2 or a polynucleotide at least 95% identical to Sequence ID NO: 2.

7. The expression vector of embodiment 2, wherein the 5' CHEF1 transcriptional regulatory DNA comprises DNA located between position 1 and position 4057 in Sequence ID NO: 2 or a polynucleotide at least 95% identical to DNA located between position 1 and position 4057 in Sequence ID NO: 2.

8. The expression vector of any one of the preceding embodiments, further comprising 3' CHEF1 transcriptional regulatory DNA.

9. The expression vector of embodiment 8, wherein the 3' CHEF1 transcriptional regulatory DNA comprises Sequence ID NO: 3 or a polynucleotide at least 95% identical to Sequence ID NO: 3.

10. The expression vector of embodiment 8, wherein the 3' CHEF1 transcriptional regulatory DNA comprises DNA located between position 1 and position 4180 in Sequence ID NO: 3 or a polynucleotide at least 95% identical to DNA located between position 1 and position 4180 in Sequence ID NO: 2.

11. The expression vector of embodiment 10, wherein the 3' CHEF1 transcriptional regulatory DNA comprises DNA located between position 1 to position 209 in Sequence ID NO: 3 or a polynucleotide at least 95% identical to DNA located between position 1 to position 209 in Sequence ID NO: 3.

12. The expression vector of any one of embodiments 8-11, wherein the 3' CHEF1 transcriptional regulatory DNA comprises about 4.2 kilobases.

13. The expression vector of any one of the preceding embodiments comprising a CMV promoter.

14. The expression vector of any one of the preceding embodiments comprising an AdTPL sequence.

15. The expression vector of any one of the preceding embodiments comprising a CMV promoter and an AdTPL sequence.

16. The expression vector of embodiment 2, wherein the 5' CHEF1 transcriptional regulatory DNA comprises DNA set out in Sequence ID NO: 1, wherein one or more bases between position 1 and position 11,716 of Sequence ID NO: 1 is/are deleted and replaced with a CMV promoter and/or an AdTPL sequence.

17. The expression vector of embodiment 16, wherein one or more bases between position 10,512 and position 11,716 of Sequence ID NO: 1 is/are deleted and replaced with a CMV promoter and/or an AdTPL sequence.

18. The expression vector of embodiment 17, wherein one or more bases between position 10,512 and position 11,716 of Sequence ID NO: 1 is/are deleted and replaced with a CMV promoter.

19. The expression vector of embodiment 17, wherein one or more bases between position 10,512 and position 11,716 of Sequence ID NO: 1 is/are deleted and replaced with an AdTPL sequence.

20. The expression vector of embodiment 17, wherein one or more bases between position 10,512 and position 11,716 of Sequence ID NO: 1 is/are deleted and replaced with a CMV promoter and an AdTPL sequence.

21. The expression vector of any one of the preceding embodiments comprising Sequence ID NO: 4 or a polynucleotide at least 95% identical to Sequence ID NO: 4.

22. The expression vector of any one of the preceding embodiments comprising Sequence ID NO: 5 or a polynucleotide at least 95% identical to Sequence ID NO: 5.

23. The expression vector of any one of the preceding embodiments comprising Sequence ID NO: 6 or a polynucleotide at least 95% identical to Sequence ID NO: 6.

24. The expression vector of any one of the preceding embodiments comprising Sequence ID NO: 7 or a polynucleotide at least 95% identical to Sequence ID NO: 7.

25. The expression vector of any one of the preceding embodiments, further comprising a selectable marker gene.

26. The expression vector of any one of the preceding embodiments, further comprising a polynucleotide encoding a protein of interest operably linked to the 5' CHEF1 transcriptional regulatory DNA, the 3' CHEF1 transcriptional regulatory DNA, the CMV promoter and/or the AdTPL sequence.

27. A host cell transformed, transduced or transfected with an expression vector according to any one of the preceding embodiments.

28. The host cell of embodiment 27, wherein the host cell is a prokaryotic cell.

29. The host cell of embodiment 27, wherein the host cell is a eukaryotic cell.

30. The host cell of embodiment 29, wherein the host cell is a hamster cell.

31. The host cell of embodiment 30, wherein the host cell is a Chinese Hamster Ovary (CHO) cell.

32. The host cell of embodiment 29, wherein the host cell is a non-hamster mammalian cell.

33. The host cell of embodiment 32, wherein the host cell is a human cell.

An expression plasmid according to the disclosure is further described in the following Example. The Example serves only to illustrate the invention and is not intended to limit the scope of the invention in any way.

EXAMPLE

Figure 2:
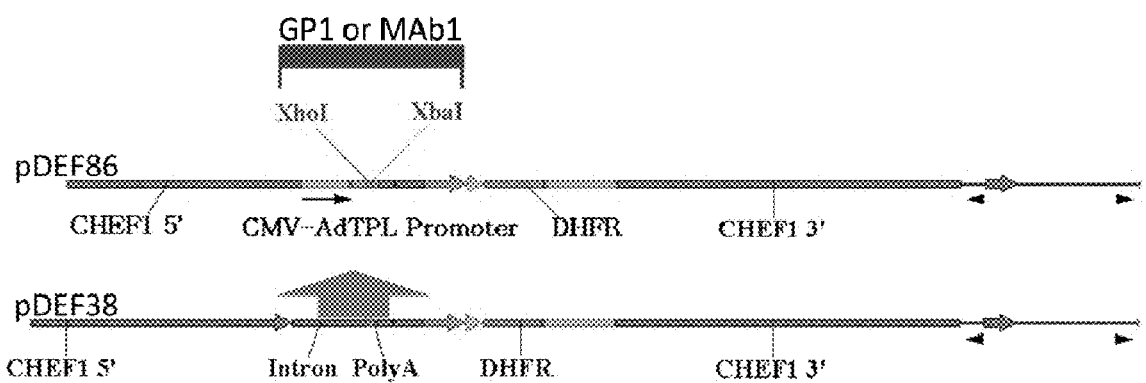
FIG. 2 shows a map of the expression vector pDEF86 comprising 5' and 3' CHEF1 transcriptional regulatory DNA, a CMV promoter, and an AdTPL sequence. The CMV promoter and AdTPL sequence replace 1217 nucleotides (from position 2866 to position 4083) of the 5' CHEF1 DNA in vector pDEF38 to create pDEF86. GP1 and MAb1 reporter genes were cloned into the XhoI-XbaI cloning sites to make the expression vectors pDEF86-GP1 and pDEF86-MAb1.

Gene Sequence and Expression Vectors—DNA fragments encoding the CMV promoter (SEQ ID NO: 4) and CMV-AdTPL promoter (SEQ ID NO: 5) were chemically synthesized and cloned into pDEF38, a CHEF1 expression vector previously described (Running Deer and Allison, 2004), creating the CHEF1-CMV-promoter vector designated pDEF85 (FIG. 1) and the CHEF1-CMV-AdTPL promoter vector designated pDEF86 (FIG. 2). Derivative vectors expressing a Fc-glycoprotein fusion (GP1) and an IgG1 antibody (MAb1) were created using standard molecular biology techniques (Maniatis et al., *J. Molecular Cloning: A Laboratory Manual*. Cold Spring Harbor Laboratory. 545, 1982) and designated pDEF38-GP1, pDEF85-GP1, pDEF86-GP1, pDEF38-MAb1, pDEF85-MAb1 and pDEF86-MAb1.

Cell Line Construction—The pDEF38-GP1, pDEF85-GP1, pDEF86-GP1, pDEF38-MAb1, pDEF85-MAb1 and pDEF86-MAb1 expression vectors were transfected individually into CHO DG44 cells by standard electroporation methods, grown for two days in non-select media containing hypoxanthine and thymidine (HT), and then selected for about two weeks in media lacking HT. The selected cell populations, or transfection pools, were expanded and split into production model cultures to assess productivity and also simultaneously split into cultures for single cell cloning.

Production Models—Small-scale fed-batch production models were run to assess culture productivity (titer) following standard biologics manufacturing processes. Cultures were inoculated at seed densities of 0.5 million cells per milliliter in shake flasks of chemically defined media (CD-CIM1, CMC Biologics, Bothell, Wash.) lacking HT. The cultures were run for 3 to 5 days at 37° C. and then shifted to lower temperatures (30° C. to 34° C.) to slow growth and promote production. Cultures were fed the supplements Balanced Feed 1 (BF1, CMC Biologics), Efficient Feed C (Feed C, Life Technologies, Grand Island, N.Y.) or Cell Boost (CB, Thermo Fisher Scientific, Waltham, Mass.) to prolong culture health. Samples for titer and cell densities were collected on Days 3, 5, 7, 10, 12, 14 and 16. The study was concluded by Day 12 to 16. Harvest supernatants were filtered through 0.2 micrometer filters and then assayed for GP1 or MAb1 production by Protein A high performance liquid chromatography (HPLC).

Cell Line Cloning—Selected GP1- and MAb1-expressing transfection pools were diluted to seed single cells into individual wells of 96-well plates. The plates were imaged from inoculation out to two weeks to identify monoclonal cell lines originating from single cells. Wells containing monoclonal colonies were expanded and either randomly chosen or selected using flow cytometry to identify highly-expressing cells from each transfection pool. Cell lines were expanded to grow in suspension culture and split into production model cultures to assess productivity.

Flow Cytometry—Fluorescence activated cell sorting (FACS) analysis was performed with Day 2 normal growing cells that were harvested and stained with fluorescent anti-IgG1 Fc antibody (RPE) to detect recombinant GP1 and MAb1 expression.

Results and Discussion

Figure 3:
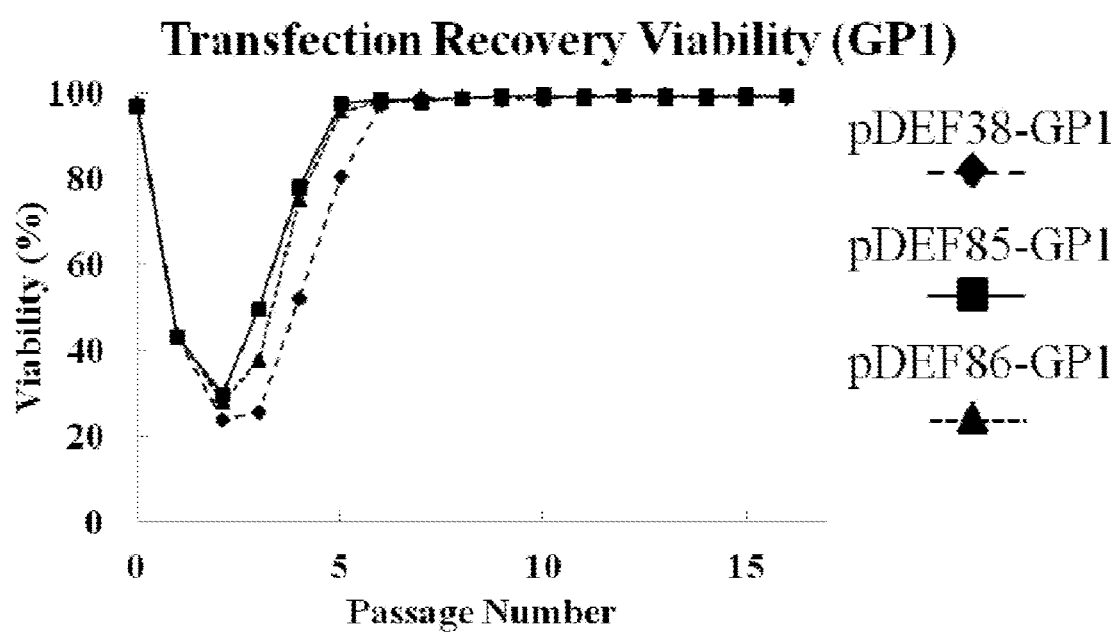
FIG. 3 shows viability of CHO host cells transfected with the vector pDEF38-GP1, pDEF85-GP1, or pDEF86-GP1. The cells recovered for 2-3 days in non-select CD-CIM1 plus HT media and were resuspended in selection media lacking HT (Passage 0). Cells were passaged every 2 to 3 days as cell number permitted. Passage number is provided on the x-axis, and percent cell viability is shown on the y-axis.

Stable cell lines expressing the reporter protein GP1 or MAb1 were made using the expression vectors pDEF38, pDEF85 and pDEF86 using standard DHFR selection methods. Transfection pools were selected in media lacking hypoxanthine and thymidine (HT) without using methotrexate. Cell viabilities dropped in media lacking HT and then recovered as cells with DHFR vectors grew out in the population. The transfection cultures dropped initially to about 10% to about 30% viability and then attained greater than 90% viability by around Day 12 (Passage 6). The growth of cells transfected with a CHEF1-CMV vector (pDEF85-GP1) or CHEF1-CMV-AdTPL vector (pDEF86-GP1) compared to cells transfected with a CHEF1 only vector (pDEF38-GP1) showed similar recovery for the GP1 expressing constructs, with consistent high viability growth after the recovery period (FIG. 3). Similar results were obtained for antibody expressing cell lines (data not shown).

Figure 4C:
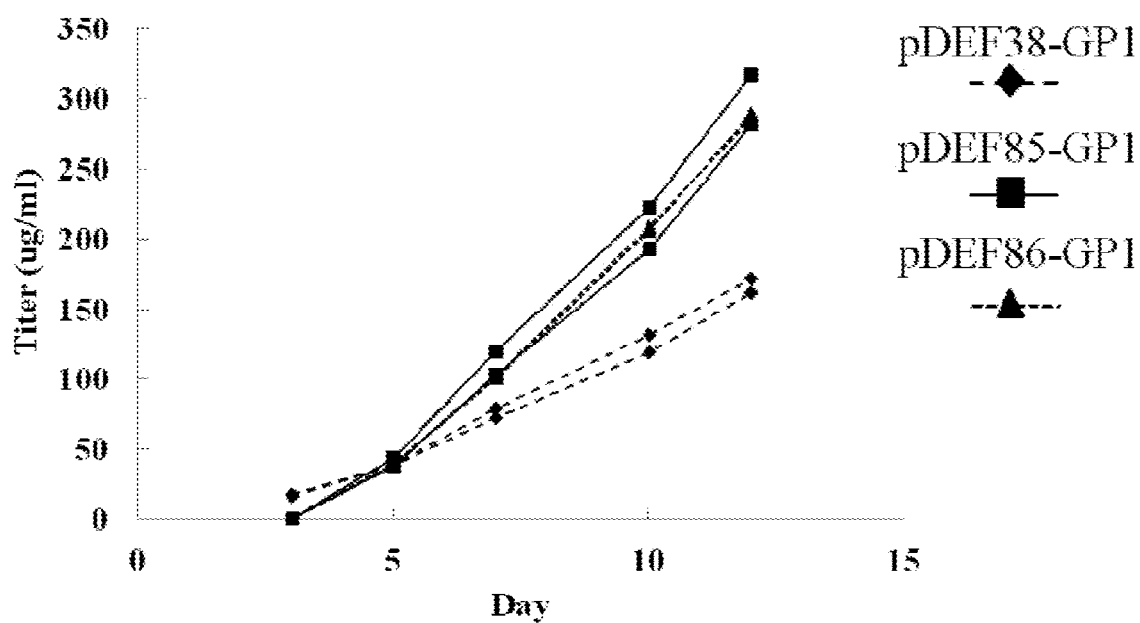
FIG. 4C shows productivity, with days shown on the x-axis and protein titer, in micrograms per milliliter, depicted on the y-axis.

Transfection pools were placed directly into production models or advanced into single cell cloning and then clonal cell lines were compared in production models. FIG. 4 shows that fed-batch shake flask production model growth was comparable for the GP1 expressing pools (FIG. 4A); however, the protein expression (titer) at harvest, typically 12 to 16 days from inoculation, was significantly different. The Day 12 harvest titers for the CHEF1-CMV or CHEF1-CMV-AdTPL expression vectors (pDEF85 and pDEF86) were much higher than for the standard CHEF1 vector (pDEF38) (FIG. 4C). The amount of recombinant GP1 protein produced from pooled transfectants in fed-batch shake flasks from the CHEF1-CMV or CHEF1-CMV-AdTPL vectors was about twice the standard CHEF1 vector. Growth of the CHEF1-CMV and CHEF1-CMV-AdTPL pools peaked slightly earlier and showed a more rapid decline in viability (FIG. 4B). The viability drop was not anticipated to improve expression and could instead be detrimental. Later experiments showed that improving ending viability increased titer for the CHEF1-CMV cultures.

Figure 5:
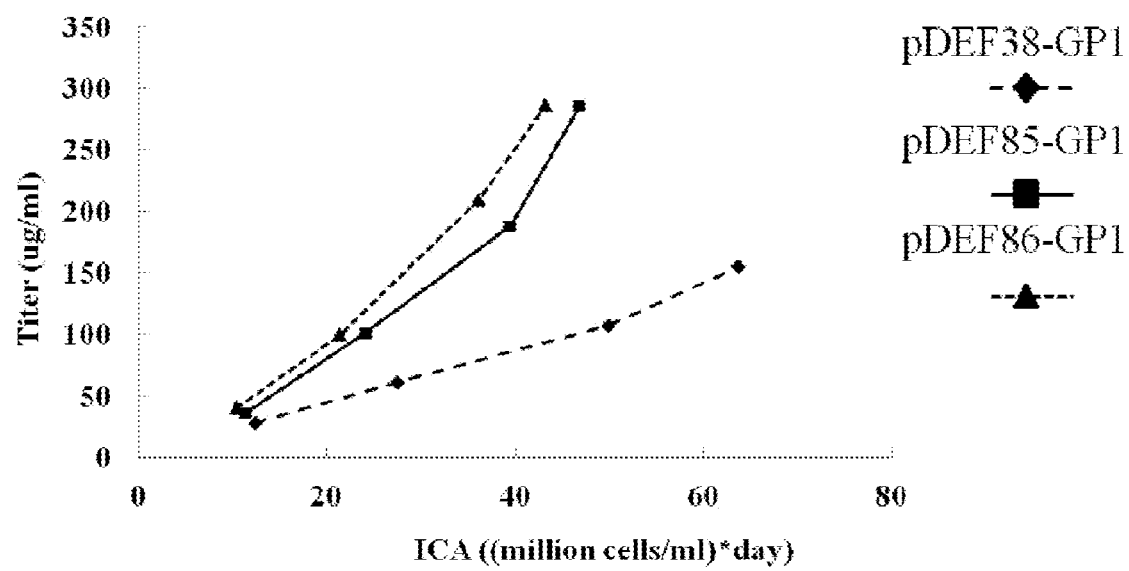
FIG. 5 shows the specific productivity of CHO host cells transfected with the vector pDEF38-GP1, pDEF85-GP1, or pDEF86-GP1. The integrated cell area (ICA), measured in million cells per milliliter multiplied by the day, is shown on the x-axis and the protein titer, measured in micrograms per milliliter, is depicted on the y-axis. The specific productivity values were calculated as picograms of protein per cell per day averaged over the entire cell culture duration.

The increase in titer seen with the CHEF1-CMV and CHEF1-CMV-AdTPL vectors was the result of increased specific productivity, as seen in FIG. 5. Specific productivity was calculated as picograms of protein per cell per day averaged over the entire culture duration. There was a slight expression difference between the CHEF1-CMV (pDEF85) and CHEF1-CMV-AdTPL (pDEF86) constructs, indicating a possible benefit of the addition of the AdTPL sequence with respect to specific productivity. The specific productivities in picograms per cell per day (PCD) are shown in Table 1. The specific productivity achieved using the CHEF1-CMV or CHEF1-CMV-AdTPL vectors was more than two-fold greater than the specific productivity of the CHEF1 vector.

TABLE 1

| | Specific Productivity | |
|---|---|---|
| Vector | Promoter | PCD |
| pDEF38 | CHEF1 | 2.4 |
| pDEF85 | CHEF1-CMV | 6.7 |
| pDEF86 | CHEF1-CMV-AdTPL | 7.4 |

Figure 6:
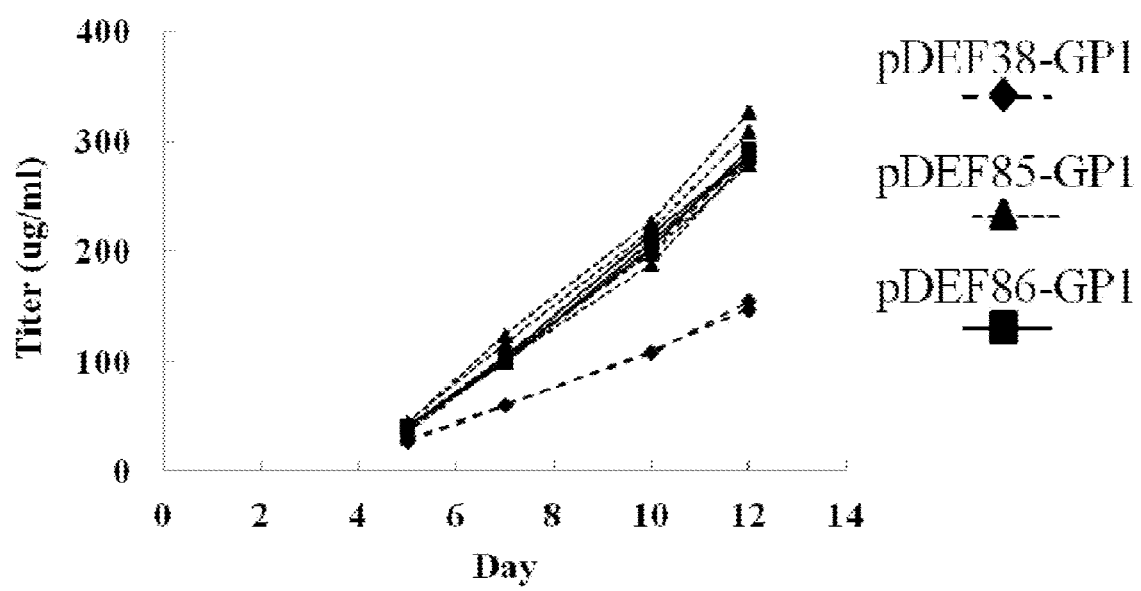
FIG. 6 shows the productivity of CHO host cells transfected with the vector pDEF38-GP1, pDEF85-GP1, or pDEF86-GP1 grown in BF1-supplemented media. Replicate transfection pools were run in 12-day fed-batch production models and fed BF1 in CD-CIM1 base media plus CB on Days 4, 6, 8, 10, and 12. Productions were run at 37° C. and shifted to 34° C. on Day 3. Titer samples were measured on Days 5, 7, 10 and 12. The days are shown on the x-axis and the protein titer, measured in micrograms per milliliter, is depicted on the y-axis.

Improved expression with the CHEF1-CMV and CHEF1-CMV-AdTPL vectors was confirmed using different reporter proteins and varied fed-batch production conditions. Cells grown in CD-CIM1 base media supplemented with CB that were fed proprietary BF1 supplement on Days 4, 6, 8, 10 and 12 demonstrated similar GP1 productivity profiles compared to cells supplemented with commercial media (Feed C). FIG. 6 shows the CHEF1-CMV and CHEF1-CMV-AdTPL vector cultures had increased GP1 titers over the control CHEF1 vector in the BF1 process.

Antibody (MAb1) production utilizing the CHEF1-CMV and CHEF1-CMV-AdTPL vectors was also tested in the BF1 process. The MAb1 transfection pools were created with the same methodology as the GP1 pools and once fully recovered from selection, were put into fed-batch shake flask production models. As shown in FIG. 7, the CHEF1-CMV and CHEF1-CMV-AdTPL MAb1 pools produced higher titer antibody than the pDEF38 controls after Day 12. The productivity profile in transfection pools expressing antibody was novel compared to glycoprotein production because the antibody productivity increased dramatically as cells entered stationary phase. A lower initial titer (Day 7) for the CHEF1-CMV and CHEF1-CMV-AdTPL MAb1 pools compared to the CHEF1 MAb1 pool was seen as the cell cultures were actively growing, followed by rapid increases in productivity for the CHEF1-CMV and CHEF1-CMV-AdTPL cultures as the growth slowed down and finally declined after Day 10 (FIG. 7B). Even as the viable cell density decreased (FIG. 7A), productivity increased out to Day 14 in the CHEF1-CMV and CHEF1-CMV-AdTPL pools, whereas it started to slow down in the CHEF1 pool, although the terminal Day 14 percent viabilities were similar for all cultures (about 80% viable, data not shown).

Clonal cultures were developed from transfection pools expressing both GP1 and MAb1. Monoclonal cell lines were identified by imaging of limiting dilution plates and then expanded into suspension culture. Twelve MAb1 clonal cultures were selected randomly from each of the pDEF38-MAb1 and pDEF85-MAb1 transfection pools and were run in fed-batch shake flask production models. Clonal CHEF1-promoter (pDEF38-MAb1) antibody production matched the transfection pool profiles, showing higher expression than the pDEF85-MAb1 clones during the growth phase and then slower production as the cultures entered stationary phase (FIG. 8B). Antibody production from the CHEF1-CMV vector (pDEF85-MAb1) clones looked very similar to the transfection pool, wherein the majority of antibody expression occurred after Day 6 after exponential growth slowed down and the cells transitioned to stationary phase (FIG. 8A).

Clonal cell lines expressing GP1 were selected using a FACS based assay to detect GP1 expression early in development. More than 100 clones from each of the pDEF38-GP1 and pDEF85-GP1 transfection pools were screened and ranked by FACS mean fluorescence. The top eight GP1-expressing cultures, based on FACS analysis from each set, were further examined in fed-batch production models using CD-CIM1 base media and BF1 feeds (FIG. 9). The average titers and specific productivities, shown in Table 2 and Table 3, indicated that expression from the CHEF1-CMV promoter (pDEF85-GP1) was much higher than from the CHEF1 promoter alone (pDEF38-GP1) and was driven by an increase in specific productivity.

TABLE 2

Average Glycoprotein Titer

|  | pDEF38-GP1 | pDEF85-GP1 |
| --- | --- | --- |
| Day 12 | 760 (n = 8) | 1199 (n = 8) |
| Day 14 | 735 (n = 8) | 1456 (n = 8) |

TABLE 3

Specific Productivity

|  | pDEF38-GP1 | pDEF85-GP1 |
| --- | --- | --- |
| Average | 6.4 (n = 8) | 15.0 (n = 8) |
| Range | 2.7 to 13.6 | 10.6 to 20.1 |

As demonstrated in the foregoing Example, novel CHEF1-CMV and CHEF1-CMV-AdTPL expression vectors increased expression of both glycoprotein and antibody in stable CHO cell transfection pools. Stable clonal cell lines derived from the CHEF1-CMV and CHEF1-CMV-AdTPL pools also showed improved protein expression compared to the CHEF1-promoter pool. Increased expression in the CHEF1-CMV and CHEF1-CMV-AdTPL clonal cell lines resulted from higher specific productivity compared to CHEF1-promoter, indicating that combining CHEF1 transcriptional regulatory DNA with a CMV promoter increased cellular expression capacity and did not just improve growth performance. The expression pattern from the CHEF1-CMV constructs differed from the CHEF1-promoter alone, with maximal expression occurring later, during the stationary phase of cell growth, indicating that regulation by the CHEF1-CMV-promoter was different than from CHEF1 alone and possessed unique recombinant protein production characteristics. The delayed temporal expression of protein from CHEF1-CMV compared to CHEF1 alone is evidence that the combined regulatory elements alter CHEF1 growth-dependent expression, thus presenting a novel mechanism to control CHEF1 protein production. The high level expression achieved from a combination of CHEF1 and CMV is unexpected considering previous findings wherein the CHEF1 promoter outperformed the CMV promoter (Running Deer and Allison, 2004). Achieving increased specific productivity, combined with the observed temporal shift in expression, is beneficial because the culture feeding conditions can be optimized for biphasic growth and production in biologic manufacturing processes. An expression vector according to the disclosure comprising CHEF1 transcriptional regulatory DNA and a CMV promoter and/or an AdTPL sequence, therefore, provides an improved option for achieving high titer and productivity in recombinant protein expression systems.

All of the compositions disclosed and claimed herein can be made and executed without undue experimentation in light of the present disclosure. While the compositions of this disclosure have been described in terms of specific embodiments, it will be apparent to those of skill in the art that variations of the compositions can be made without departing from the concept and scope of the disclosure. More specifically, it will be apparent that certain polynucleotides which are both chemically and biologically related may be substituted for the polynucleotides described herein with the same or similar results achieved. All such similar substitutes and modifications apparent to those skilled in the art are deemed to be within the scope and concept of the invention as defined by the appended claims.

The references cited herein throughout, to the extent that they provide exemplary procedural or other details supplementary to those set forth herein, are all specifically incorporated herein by reference.

What is claimed:

1. An expression vector comprising Chinese Hamster Elongation Factor-1α (CHEF1) transcriptional regulatory DNA and a cytomegalovirus (CMV) promoter and/or an adenovirus tripartite leader (AdTPL) sequence, wherein the CHEF1 transcriptional regulatory DNA comprises Sequence ID NO: 1.

2. An expression vector comprising Chinese Hamster Elongation Factor-1α (CHEF1) transcriptional regulatory DNA and a cytomegalovirus (CMV) promoter and/or an adenovirus tripartite leader (AdTPL) sequence, wherein the CHEF1 transcriptional regulatory DNA comprises Sequence ID NO: 2.

3. The expression vector of claim 2, further comprising Sequence ID NO: 3.

4. An expression vector comprising Chinese Hamster Elongation Factor-1α (CHEF1) transcriptional regulatory DNA and a cytomegalovirus (CMV) promoter and/or an adenovirus tripartite leader (AdTPL) sequence, wherein the CHEF1 transcriptional regulatory DNA comprises Sequence ID NO: 3.

5. The expression vector of claim 2 comprising a CMV promoter.

6. The expression vector of claim 2 comprising an AdTPL sequence.

7. The expression vector of claim 2 comprising a CMV promoter and an AdTPL sequence.

8. The expression vector of claim 2 comprising Sequence ID NO: 4.

9. The expression vector of claim 2 comprising Sequence ID NO: 5.

10. The expression vector of claim 2 comprising Sequence ID NO: 6.

11. The expression vector of claim 2 comprising Sequence ID NO: 7.

12. The expression vector of claim 2, further comprising a selectable marker gene.

13. The expression vector of claim 2, further comprising a polynucleotide encoding a protein of interest operably linked to the CHEF1 transcriptional regulatory DNA, the CMV promoter and/or the AdTPL sequence.

14. A host cell transformed, transduced or transfected with an expression vector according to claim 2.

15. The host cell of claim 14, wherein the host cell is a prokaryotic cell.

16. The host cell of claim 14, wherein the host cell is a eukaryotic cell.

17. The host cell of claim 16, wherein the host cell is a hamster cell.

18. The host cell of claim 17, wherein the host cell is a Chinese Hamster Ovary (CHO) cell.

19. The host cell of claim 16, wherein the host cell is a non-hamster mammalian cell.

20. The host cell of claim 19, wherein the host cell is a human cell.

* * * * *